United States Patent [19]

Kise et al.

[11] Patent Number: 4,769,384
[45] Date of Patent: Sep. 6, 1988

[54] BENZIMIDAZOLE DERIVATIVES

[75] Inventors: Masahiro Kise, Kyoto; Fusao Ueda, Notogawacho; Shinichi Tada, Omihachimanshi; Masao Murase, Kusatsushi; Katsutoshi Kunimoto, Notogawacho; Makoto Sugiyama, Kyoto

[73] Assignee: Nippon Shinyaku Co. Ltd., Japan

[21] Appl. No.: 881,647

[22] Filed: Jul. 3, 1986

[30] Foreign Application Priority Data

Jul. 3, 1985 [JP] Japan .................. 60-146925

[51] Int. Cl.$^4$ .................. A61K 31/415; C07D 231/54
[52] U.S. Cl. .................. 514/394; 546/199; 546/271; 548/325; 548/329; 548/333
[58] Field of Search .................. 548/325, 333, 329; 514/394, 395

[56] References Cited

U.S. PATENT DOCUMENTS

| | | | |
|---|---|---|---|
| 2,170,474 | 8/1939 | Graenacher et al. | 548/325 X |
| 3,075,991 | 1/1963 | Moyle et al. | 548/325 |
| 3,152,142 | 10/1964 | Moyle et al. | 548/325 |
| 3,652,580 | 3/1972 | Janiak et al. | 548/325 X |
| 3,726,684 | 4/1973 | Riester et al. | 548/325 X |

FOREIGN PATENT DOCUMENTS

| | | | |
|---|---|---|---|
| 2427404 | 1/1975 | Fed. Rep. of Germany | 548/325 |
| 1576989 | 8/1969 | France | 548/325 |
| 1244762 | 9/1971 | United Kingdom | 548/325 |

Primary Examiner—Joseph Paul Brust
Attorney, Agent, or Firm—Jacobs & Jacobs

[57] ABSTRACT

Benzimidazole derivatives of the formula (I):

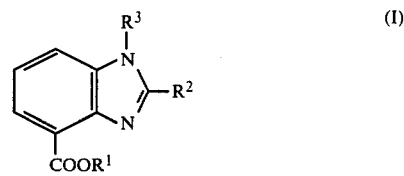

or a pharmaceutically acceptable acid addition salt thereof wherein $R^1$ is hydrogen or lower alkyl; $R^2$ is

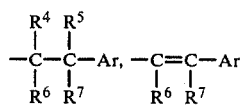

or —C≡C—Ar wherein Ar is phenyl unsubstituted or substituted by one to three substituents selected from the group consisting of halo, lower alkyl, hydroxy, unsubstituted or substituted lower alkoxy, aralkyloxy wherein the alkyl moiety is a lower alkyl moiety, lower alkenyloxy, lower alkynyloxy, difluoromethoxy, lower alkylamino, methylenedioxy, trifluoromethyl, cyano, lower alkylthio and lower alkylsulfinyl; $R^4$, $R^5$, $R^6$ and $R^7$ a hydrogen or lower alkyl or $R^4$ and $R^5$ together with the carbon atoms to which they are attached form a cyclopropyl ring; and $R^3$ is hydrogen, lower alkyl, acyl or lower alkylsulphonyl are useful in the treatment of ulcers of the stomach and duodenum in humans and animals.

24 Claims, No Drawings

BENZIMIDAZOLE DERIVATIVES

The present invention is concerned with Benzimidazole derivatives and pharmaceutically acceptable acid addition salts thereof which are useful for their anti-ulcer activity in humans and animals.

Anti-ulcer agents known in the art generally comprise antacids and anti-cholinergic agents. These, unfortunately, have the disadvantage that administration of sufficient doses to inhibit gastric juice secretion cause side effects. Histamine $H_2$ antagonists have been used but also exhibit disadvantages and lack the curative effect.

Among benzimidazole derivatives, omeprazole and H-149/94 (see Japanese Laid Open Specification No. 54/141783) have been described as inhibitors of gastric secretion.

According to the present invention, compounds of the formula (I):

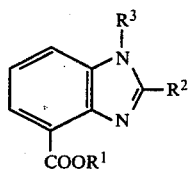

or a pharmaceutically acceptable acid addition salt thereof wherein $R^1$ is hydrogen or lower alkyl; $R^2$ is

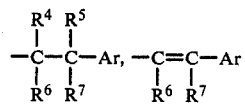

or —C≡C—Ar wherein Ar is phenyl unsubstituted or substituted by one to three substituents selected from the group consisting of halo, lower alkyl, hydroxy, straight or branched chain lower alkoxy, unsubstituted or substituted by lower alkoxy especially branched chain of 1 to 4 carbon atoms, acetyloxy, amino, mono- or di-lower alkylamino, piperidino or 2-pyridinyl, aralkyloxy wherein the alkyl moiety is a lower alkyl moiety, lower alkenyloxy, lower alkynyloxy, difluoromethoxy, lower alkylamino, methylenedioxy, trifluoromethyl, cyano, lower alkylthio and lower alkylsulfinyl; $R^4$, $R^5$, $R^6$ and $R^7$ are hydrogen or lower alkyl or $R^4$ and $R^5$ together with the carbon atoms to which they are attached form a cyclopropyl ring; and $R^3$ is hydrogen, lower alkyl, acyl or lower alkylsulphonyl have been discovered which exhibit better anti-ulcer activity than those compounds heretofore known without the adverse contraindications. The compounds of the present invention are particularly useful for ulcers of the stomach and duodenum.

When $R^1$ according to the present invention is lower alkyl, it is preferred that the alkyl group be straight or branched chain of 1 to 4 carbon atoms, particularly methyl, ethyl, n-propyl, isopropyl, n-butyl, isobutyl, sec-butyl or tert-butyl.

When $R^4$, $R^5$, $R^6$, and $R^7$ are lower alkyl, it is preferred that the alkyl group be straight or branched chain of 1 to 4 carbon atoms, particularly methyl, ethyl, n-propyl, isopropyl, n-butyl, isobutyl, sec-butyl or tert-butyl.

Preferred substituents for the phenyl group of Ar include fluoro, chloro, bromo, iodo, straight or branched chain alkyl of 1 to 4 carbon atoms, straight or branched chain alkoxy of 1 to 4 carbon atoms unsubstituted or substituted by lower alkoxy especially branched chain of 1 to 4 carbon atoms, acetyloxy, amino, mono- or di-lower alkylamino, piperdino or 2-pyridinyl.

Preferred alkyl moieties in the above substituents include methyl, ethyl, n-propyl, isopropyl, n-butyl, isobutyl, sec-butyl and tert-butyl.

Aralkyloxy is preferably of 7 to 9 carbon atoms, for exaple benzyloxy, phenethyloxy, phenylpropyloxy, alpha-methylbenzyloxy and beta-methyl-phenethyloxy.

Alkenyloxy is preferably straight or branched chain of 3 to 6 carbon atoms, particularly allyl, isopropenyl, 2-methallyl, 2-butenyl and 3-butenyl.

Alkynyloxy is preferably straight or branched chain of 3 to 6 carbon atoms, particularly 2-propynyloxy, 2-butynyloxy, 2-heptynyloxy, 2-hexynyloxy, alpha-methyl-2-propynyloxy, alphamethyl-2-butynyloxy, alpha-methyl-2-heptynyloxy, 3-butynyloxy, 3-heptynyloxy and 3-hexynyloxy.

The alkylamino moieties are preferably those of 1 to 4 carbon atoms, particularly methylamino, dimethylamino, ethylamino, diethylamino, n-propylamino, di-n-propylamino, di-isopropylamino and di-n-butylamino.

Alkylthio is preferably of 1 to 4 carbon atoms, particularly methylthio, ethylthio, n-propylthio, isopropylthio and n-butylthio.

Alkylsulfinyl is preferably of 1 to 4 carbon atoms, particularly methylsulfinyl, ethylsulfinyl, n-propylsulfinyl, isopropylsulfinyl and n-butylsulfinyl.

When $R^2$ contains isomers, they may be either cis or trans. The trans form is preferred.

When $R^3$ is lower alkyl, it is preferred that the alkyl group be straight or branched chain of 1 to 4 carbon atoms, particularly methyl, ethyl, n-propyl, isopropyl, n-butyl, isobutyl, sec-butyl or tert-butyl. When it is acyl, those moieties of 2 to 4 carbon atoms are preferred, particularly acetyl, propionyl and butyryl. When $R^3$ is alkylsulfonyl, it is preferably of 1 to 4 carbon atoms, particularly methanesulfonyl, ethanesulfonyl, propanesulfonyl and butanesulfonyl.

The compounds of formula (I) can be produced as follows:

(Step 1)

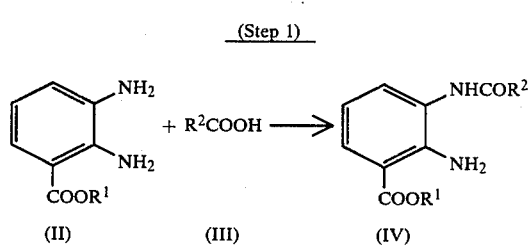

(Step 2)

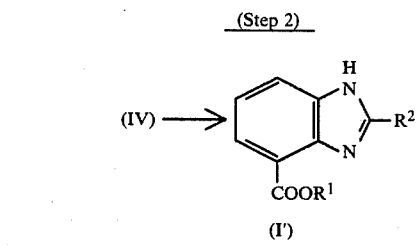

wherein $R^1$ and $R^2$ are as above defined excluding, in those reactions given above, the case where $R^1$ is hydrogen.

The reaction of (II) with (III) may be conducted by any procedure per se known, such as, for example, mixed anhydride or dicyclohexylcarbodiimide. In addition, the use of reactive derivatives of (III) such as, for example, acid anhydride, acid halide, activated ester, etc. may be also give the compound (IV). For example, in the reaction in which a mixed acid anhydride is used, the compound (II) is made to react with a little more of the compound (III) than the equivalent amount in the presence of alkyl chlorocarbonate (such as, for example, methyl chlorocarbonate, ethyl chlorocarbonate and isopropyl chlorocarbonate) and a base (such as, for example, triethylamine). The reaction is usually carried out in an inert solvent (such as, for example, chloroform, methylene chloride, etc.) at 0° C. to ambient temperature. The reaction time varies depending upon the compounds (II) and (III) applied and also upon the reaction temperature for usually 3 to 48 hours, preferably 15 to 20 hours. Then ring closure of (IV) is effected to produce (I'). Said ring closure reaction is carried out in a polar solvent (such as, for example, water and methanol) by heating at 100°–150° C. or by refluxing using a great excess of known acid (such as, for example, acetic acid, sulfuric acid, hydrochloric acid, and polyphosphoric acid). Though the reaction time varies depending upon the compound (IV) and the acid applied and also upon the reaction temperature, it is usually 1 to B 20 hours. It is also possible to produce compounds of the formula (I) directly without isolating the compound (IV) in a route of from Step 1 to Step 2. Thus, the compound (II) is heated at 100°–150° C. or refluxed in a great excess of polyphosphoric acid, polyphosphate, hydrochloric acid or sulfuric acid to manufacture the compound (I).

If desired, the compound (I') is hydrolyzed to afford the corresponding carboxylic acid. Said hydrolysis reaction can be easily carried out in, for example, water, methanol, ethanol or a mixture thereof by the use of an alkali such as, for example, sodium hydroxide or potassium hydroxide. The reaction is usually conducted at 0° C. to 150° C. and, more preferably, at 20° C. to 100° C. The amount of the alkali is 1 to 5 moles, more preferably 2 to 4 moles, to 1 mole of the compound (I').

If desired, the compound (I') is subjected to an N-alkylation, N-acylation or N-alkylsulfonylation to afford the corresponding N-substituted benzimidazole derivatives.

Examples of the N-alkylating methods are known and are, for example, the reaction with alkyl halide, that with alkyl sulfate (such as dimethyl sulfate) or with sulfonate, or the reductive alkylation using an aldehyde. The reaction conditions may vary depending upon the starting materials and the alkylating agents applied and, in accordance with the desired final product, suitable combination of the reaction temperature, reaction time, and the solvent is selected. For example, in the manufacture of the N-methyl compound using alkyl halide, the alkyl halide is applied in a suitable solvent (polar and aprotic solvent such as tetrahydrofuran or N,N-dimethylformamide) in the presence of a base such as, for example, sodium hydride, potassium hydride, triethylamine or diazabicycloundecene (DBU). Usually the reaction temperature is 0° to 60° C. and there are many cases where the reaction is conducted with cooling or at room temperature. Though the reaction time may vary depending upon the starting material and alkyl halide applied, it is usually 1 hour to around 40–60 hours.

As to methods of the N-acylation, there are several known methods including a method wherein a carboxylic acid is combined using a combining agent (such as, for example, carbodiimides, tetrachlorosilane/anhydrous pyridine, and titanium chloride), a method wherein acid halide is used in the presence of a base (such as, for example, tertiary amine, sodium hydroxide, sodium acetate, and alkali carbonate), and a method wherein an acid anhydride is used in the presence of a reaction accelerator (such as, for example, sulfuric acid or sodium acetate) if desired.

The reaction condition may vary depending upon the starting material and acylating agent used and, in accordance with the aimed compound, suitable combination of reaction temperature, reaction time, and solvent is selected. For example, N-acetyl derivatives are obtained by the reaction with acetyl chloride in suitable solvent (such as, for example, tetrahydrofuran, N,N-dimethylformamide, etc.) in the presence of triethylamine.

The reaction temperature is usually 0° to 60° C. and, more preferably, it is room temperature. Reaction time varies depending upon the starting material, reaction temperature and solvent used and, usually, the reaction completes from 1 hour to around 50 hours.

As to a method for N-alkylsulfonylation, conventional methods such as, for example, that using alkylsulfonyl chloride are applied by the similar way as in the above-given acylation method.

N-substituted benzimidazole derivatives may also be manufactured by the monoalkylation, monoacylation or monoalkylsulfonylation of the starting material (II) followed by reacting with the compound (III).

Among the compounds produced in accordance with the above methods, those having styryl group as $R^2$ may, if desired, be subjected to a catalytic reduction to afford the corresponding phenethyl compounds. Such a catalytic reduction is carried out at ordinary temperature and pressure in a suitable solvent such as, for example, alcohol, ethyl acetate, tetrahydrofuran, etc. in the presence of a catalyst such as, for example, palladium-carbon, cadmium-carbon, etc. Though the reaction time may vary according to the compound used, it is usually 10 to 20 hours.

When $R^2$ contains styryl groups in the compounds produced above, they are, if desired, subjected to a photoreaction to give the corresponding isomers. Such as photoreaction is conducted by irradiating with a light from tungsten lamp for two days to one week in a solvent which does not absorb light such as, for example, methanol, ethanol, ethyl acetate, ether, etc. After the reaction, desired compounds can be isolated by silica gel column chromatography.

Compounds of the formula (I) having a basic group can be made into pharmaceutically acceptable acid addition salts by procedures per se known. Preferred salts are, for example, salts with mineral acids such as, for example, hydrochloric acid, sulfuric acid, nitric acid, phosphoric acid, boric acid, hydrobromic acid and the like and such salts with organic acids such as, for example, benzenesulfonic acid, p-toluenesulfonic acid, methanesulfonic acid, ethanesulfonic acid, naphthalenesulfonic acid, camphorsulfonic acid and the like.

Compounds of the formula (I) and said salts thereof may be isolated from the reaction mixture by a usual separation-purification means such as, for example, extraction, concentration, neutralization, filtration, recrystallization, column chromatography, thin layer chromatography, and the like.

Starting materials (II) used in the present invention may be produced by known methods (cf. Can. J. Chem. 55, 1653, 1977) or other methods similar thereto. Also, they are produced by the following method:

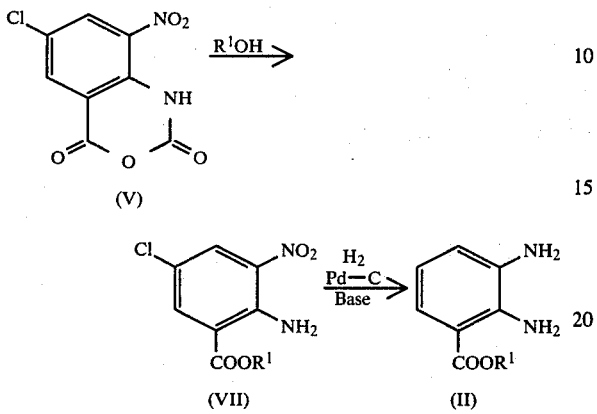

wherein $R^1$ is as above defined.

Another starting material (III) is either a known compound or can be manufactured by a known method per se.

In accordance with the above scheme, 5-chloro-3-nitroisatonic anhydride (V) which is a known compound is used as a starting material.

The compound (V) is heated in alcohol of the formula $R^1OH$ wherein $R^1$ is as above defined, water or aqueous solution of alkali whereupon the ring is opened giving (VII). The resulting (VII) is subjected to a catalytic reduction by a known manner such as, for example, by reducing with palladium carbon in the presence of a base to give (II).

The anti-ulcer activity and the acute toxicity of the compounds and pharmaceutically acceptable acid addition salts of the present invention are demonstrated by the tests described below:

Anti-ulcer Action

Biological test method: Male rats of seven weeks of age were fasted for 24 hours and subjected to the test.

The compound to be tested was suspended in a physiological saline solution containing 0.5% methylcellulose therein. 10 ml/kg of it was administered orally. The animals were immediately placed in a stress cage and immersed in a water bath of 23° C. to the depth of xiphoid. After 17 hours, they were sacrificed by cervical dislocation. The stomach was isolated therefrom. 7 ml of 2% formaline solution was introduced into the stomach for fixation. Then the stomach was cut along a greater curvature. The length of ulcer produced in fundus was measured under a microscope and the total ulcer length (in mm) was defined as an ulcer index per rat. Significance between mean ulcer indices was verified by the Student t-test.

Results: The results are shown in Table 1.

TABLE 1

| Compound (designated by example number) | Dose (per os) mg/kg | Antiulcer Action (inhibition %) after 17 hours |
| --- | --- | --- |
| 1 | 10 | 40** |
|   | 20 | 78*** |
|   | 40 | 97*** |

TABLE 1-continued

| Compound (designated by example number) | Dose (per os) mg/kg | Antiulcer Action (inhibition %) after 17 hours |
| --- | --- | --- |
| 1 (phosphate) | 10# | 66*** |
|   | 20# | 92*** |
| 14 | 20 | 26 |
|   | 40 | 81*** |
|   | 80 | 96*** |
| 30 | 20# | 44 |
|   | 40# | 55* |
|   | 80# | 82* |
| 53 | 20# | 81*** |
|   | 40# | 99*** |
|   | 80# | 99*** |
| 54 | 20# | 55** |
|   | 40# | 86*** |
|   | 80# | 98*** |
| 65 | 5# | 12 |
|   | 10# | 69* |
|   | 20# | 89*** |
| 66 | 5# | 7 |
|   | 10# | 63** |
|   | 20# | 87*** |
| 67 | 5# | 48* |
|   | 10# | 72** |
| 69 | 5# | 38** |
|   | 10# | 82*** |
| 70 | 5# | 3 |
|   | 10# | 72** |
|   | 20# | 80*** |
| 86 | 5# | 4 |
|   | 10# | 35* |
|   | 20# | 98*** |
| Cimetidine | 200 | 66* |

Note:
*$p < 0.05$, $p < 0.01$, *$p < 0.001$
Dose of the acid-addition salt is that as the corresponding base.

Acute Toxicity

Method: Male mice of six weeks of age or male rats of six weeks of age were fasted for 24 hours and subjected to the test.

The compound to be tested was suspended in physiological saline solution containing 0.5% of methylcellulose. The suspension was administered orally. The animals were fed by the usual manner and the general symptoms including the death of them were observed for two weeks.

Results: The test results are shown in Table 2 below.

TABLE 2

| Compound (designated by Example Number) | Dose (p.o.) mg/kg | Animals Used | Death Ratio |
| --- | --- | --- | --- |
| 1 | 2000 | Mice | 0/5 |
|   |   | Rats | 1/4 |
| 1 (phosphate) | 2580 | Mice | 0/3 |
|   |   | Rats | 0/4 |
| 14 | 2000 | Rats | 0/4 |
| 54 | 2636 | Rats | 0/4 |
| 65 | 3440 | Mice | 2/5 |
| 69 | 2560 | Mice | 2/5 |
| 70 | 2340 | Mice | 1/5 |
| 86 | 2280 | Rats | 0/3 |

The above results demonstrate that the compounds and salts of the present invention exhibit anti-ulcer activity and show low toxicity. Accordingly, they are useful for the treatment of peptic ulcers in humans and animals.

The compounds of the present invention and their pharmaceutically acceptable salts may be formulated into pharmaceutical compositions using techniques per se known. Pharmaceutical compositions may thus be prepared which are useful for administration to humans and animals suffering from peptic ulcers. Such compositions are produced by combining a therapeutically effective amount of a compound of the formula (I) or a pharmaceutically acceptable acid addition salt thereof with a pharmaceutically acceptable carrier.

The present invention also includes methods of treating ulcers in humans and animals which comprises administering a therapeutically effective amount of a compound of the formula (I) or a pharmaceutically acceptable acid addition salt thereof in combination with a pharmaceutically acceptable carrier.

Suitable pharmaceutical compositions according to the present invention may contain from 0.1% to 99.5% of a compound of the formula (I) or a pharmaceutically acceptable acid addition salt thereof or more preferably from about 0.5 to about 90%. Such pharmaceutical compositions are preferably in dosage unit form; i.e., physically discrete units containing a predetermined amount of the compound of the formula (I) or a pharmaceutically acceptable acid addition salt thereof corresponding to a fraction or multiple of the dose which is calculated to produce the desired therapeutic response. The dosage units can contain one, two three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day.

Although the dosage and dosage regimen must in each case be carefully adjusted, utilizing sound professional judgment and considering the age, weight and condition of the recipient, the route of administration and the nature and gravity of the illness, generally the dosage will be as follows: for oral administration from about 1 to about 3000 mg one to three times per day of said compound or salt thereof for an average human adult, preferably 20 to 150 mg per day. For parenteral administration, from about 0.1 to about 50 mg three to four times per day. For rectal administration, from about 1 to about 500 mg one to three times per day. In some instances, a sufficient therapeutic effect can be obtained at a lower dose, while in others a larger dose will be required. Oral administration is particularly preferred.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder as carboxymethyl cellulose, an alginage, gelatin, or polyvinyl pyrrolidone, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearic salt, talc or mineral oil. The lubricated mixture is then compressed into tablets. The compounds and pharmaceutically acceptable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterline solutions and suspensions intended for subcutaneous, intramuscular or intravenous injection. These are prepared by suspending or dissolving a measured amount of the compound in a non-toxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

The compositions and methods of the present invention are particularly useful for oral administration.

The following non-limitative examples more particularly illustrative the present invention:

Reference Example 1

(1) Methyl 5-chloro-3-nitroanthranilate

To 1.5 liter of methanol was added 150 g of 5-chloro-3-nitroisatonic anhydride and the mixture was refluxed for 6 hours with stirring. The reaction solution was allowed to cool to room temperature and crystals separated out were collected by filtration. Yellowish orange crystals, m.p. 110°–111° C. The yield 133.6 g.

(2) Methyl 2,3-diaminobenzoate

A mixture of 5 g 5% palladium-carbon, 2.8 liters of methanol, 59 g of potassium acetate (anhydride), and 138.4 g methyl 5-chloro-3-nitroanthranilate was subjected to hydrogen absorption with stirring and cooling with a water bath. When the hydrogen absorption was completed, the reaction mixture was filtered, and the filtrate was concentrated in vacuo. To the residue were added ice and 1 lit mixture of n-hexane:ethyl acetate (6:4) and separated. The organic solvent layer was washed with saturated sodium bicarbonate solution, then washed with saturated sodium chloride solution, dried with anhydrous magnesium sulfate, and concentrated in vacuo to give dark brown crystals, m.p. 59°–61° C.

EXAMPLE 1

(1) Methyl 2-amino-3-(3,4-dimethoxycinnamoyl)aminobenzoate 3,4-Dimethoxycinnamic acid (87.45 g) was suspended in 400 ml chloroform, 62 ml triethylamine was added with ice-cooling and stirring and, after the latter was dissolved, 43.41 g ethyl chlorocarbonate was added. The mixture was stirred for 1 hour with ice-cooling, a mixture of 66.47 g methyl 2,3-diaminobenzoate and 200 ml chloroform was gradually dropped in and stirred overnight on a water bath. After the reaction, the reaction solution was washed with saturated aqueous solution of sodium bicarbonate and sodium chloride solution, dried over anhydrous magnesium sulfate, concentrated in vacuo, 300 ml methanol was added to the residue, the mixture was refluxed for 20 hours, cooled, insoluble matter was collected by filtration, air-dried, and 106.5 g of grayish white crystals were obtained. Recrystallization from ethanol gave grayish white crystals of m.p. 190°–191.5° C.

Elem. Anal. ($C_{19}H_{20}N_2O_5$). Calcd (%): C: 64.04 H: 5.66 N: 7.86. Found (%): C: 63.94 H: 5.57 N: 7.87.

IR (KBr) cm$^{-1}$: 3480, 3370, 1698, 1260, 1140, 760.

(2) Methyl (E)-2-(3,4-dimethoxystyryl)benzimidazole-4-carboxylate

Methyl 2-amino-3-(3,4-dimethoxycinnamoyl)aminobenzoate (94 g) obtained in (1) was refluxed for 3 hours with 500 ml acetic acid with stirring. After the reaction, acetic acid was evaporated in vacuo, the residue was dissolved in chloroform, the solution was washed with saturated aqueous solution of sodium bicarbonate and then with water, dried with anhydrous magnesium sulfate, chloroform was evaporated, the dark brown oily residue was dissolved in ethyl acetate, ether was added to the solution, allowed to stand, crystals separated out was collected by filtration, and air-dried to give 79.6 g of cyrstals. Recrystallization from a mixture of ethyl acetate and ether gave yellow crystals of m.p. 144°–146° C.

Elem. Anal. ($C_{19}H_{18}N_2O_4$). Calcd (%): C: 67.45 H: 5.36 N: 8.28. Found (%): C: 67.35 H: 5.39 N: 8.25.

IR (KBr) cm$^{-1}$: 3500~2500, 3420, 1725, 1280, 1145, 750.

NMR (CDCl$_3$) δ: 3.92 (3H, s), 3.95 (3H, s), 4.02 (3H, s), 6.89 (1H, d, J=8 Hz), 7.02 (1H, d, J=16 Hz), 7.12 (1H, d, J=1.5 Hz), 7.14 (1H, dd, J=8 Hz, 1.5 Hz), 7.28 (1H, t, J=8 Hz), 7.58 (1H, d, J=16 Hz), 7.85 (1H, dd, J=8 Hz, 1.5 Hz), 7.92 (1H, dd, J=8 Hz, 1.5 Hz), 10.32~10.44 (1H, broad).

(3) Methyl (E)-2-(3,4-dimethoxystyryl)benzimidazole-4-carboxylate (4.0 g) obtained in the above (2) was dissolved in 30 ml methanol and a mixture of 1.36 g of equimolar phosphoric acid (85% concentration) and 20 ml methanol was added with stirring at room temperature. The resulting precipitate was collected by filtration, well washed with methanol, ether, and dried in vacuo at 70° C. for 10 hours to give 4.37 g (85%) of phosphate. Phosphate m.p. 284°–289° C.

Elem. Anal. ($C_{19}H_{18}N_2O_4 \cdot H_3PO_4$). Calcd (%): C: 52.30 H: 4.85 N: 6.42. Found (%): C: 52.23 H: 4.89 N: 6.47.

NMR (DMSO-d$_6$) δ: 3.82 (3H, s), 3.86 (3H, s), 3.98 (3H, s), 7.03 (1H, d, J=8 Hz), 7.17–7.38 (4H, m), 7.75–7.94 (3H, m), 12.10–12.50 (4H, br).

By the similar manner as Example 1, compounds of Example 2 and thereafter were manufactured.

EXAMPLE 2

Methyl (E)-2-(4-trifluoromethylstyryl)benzimidazole-4-carboxylate

M.p. 137.5°–139° C. (recrystallized from benzene).

Elem. Anal. ($C_{18}H_{13}F_3N_2O_2$). Calcd (%): C: 62.43 H: 3.78 N: 8.09 F: 16.46. Found (%): C: 62.61 H: 3.64 N: 8.14 F: 16.58.

IR (KBr) cm$^{-1}$: 3500~2600, 3410, 1695, 1280, 1155, 755.

NMR (CDCl$_3$) δ: 4.01 (3H, s), 7.21 (1H, d, J=16 Hz), 7.28~7.35 (1H, m), 7.62 (4H, s), 7.69 (1H, d, J=16 Hz), 7.88~7.98 (2H, m), 10.0~11.5 (1H, br).

EXAMPLE 3

Methyl (E)-2-(3,4,5-trimethoxystyryl)benzimidazole-4-carboxylate

M.p. 154.0°–155.5° C. (recrystallized from benzene).

Elem. Anal. ($C_{20}H_{20}N_2O_5 \cdot \frac{1}{4}H_2O$). Calcd (%): C: 64.42 H: 5.47 N: 7.51. Found (%): C: 64.37 H: 5.59 N: 7.52.

IR (KBr) cm$^{-1}$: 3500~2600, 3360, 1730, 1285, 1130, 820.

NMR (CDCl$_3$) δ: 3.89 (3H, s), 3.90 (6H, s), 4.01 (3H, s), 6.79 (2H, s), 7.08 (1H, d, J=16 Hz), 7.26~7.34 (1H, m), 7.58 (1H, d, J=16 Hz), 7.86~7.96 (2H, m) 10.0~11.5 (1H, br).

EXAMPLE 4

Methyl (E)-2-[4-(N,N-diethylamino)styryl]benzimidazole-4-carboxylate

M.p. 140°–142° C. (recrystallized from benzene).

Elem. Anal. (C₂₁H₂₃N₃O₂). Calcd (%): C: 72.18 H: 6.63 N: 12.03. Found (%): C: 72.07 H: 6.68 N: 11.89.

IR (KBr) cm⁻¹: 3500~2600, 3440, 1720, 1700, 1280, 1140, 760.

NMR (CDCl₃) δ: 1.19 (6H, t, J=7 Hz), 3.39 (4H, q, J=7 Hz), 4.01 (3H, s), 6.65~6.71 (2H, m), 6.89 (1H, d, J=16 Hz), 7.21~7.29 (1H, m), 7.36~7.48 (2H, m), 7.56 (1H, d, J=16 Hz), 7.80~7.92 (2H, m), 10.0~10.4 (1H, br).

Hydrochloride m.p. 213°–214° C.

Elem. Anal. (C₂₁H₂₄ClN₃O₂·H₂O). Calcd (%): C: 62.45 H: 6.49 N: 10.40 Cl: 8.78. Found (%): C: 62.64 H: 6.57 N: 10.49 Cl: 8.90.

IR (KBr) cm⁻¹: 3500~2600, 3450, 1720, 1280, 1160, 760.

NMR (CDCl₃) δ: 1.17 (6H, t, J=7 Hz), 3.34 (4H, q, J=7 Hz), 4.14 (3H, s), 7.06–7.40 (H, m), 7.78–7.88 (1H, m), 7.92–8.04 (1H, m), 8.10–8.30 (1H, m) 11.0–13.0 (1H, br).

EXAMPLE 5

Methyl (E)-2-(3,4-methylenedioxystyryl)benzimidazole-4-carboxylate

M.p. 173°–175° C. (benzene).

Elem. Anal. (C₁₈H₁₄N₂O₄·½H₂O). Calcd (%): C: 65.85 H: 4.50 N: 8.53. Found (%): C: 65.68 H: 4.46 N: 8.25.

IR (KBr) cm⁻¹: 3500~2600, 1710, 1290, 1145, 760.

NMR (CDCl₃) δ: 4.02 (3H, s), 6.00 (2H, s), 6.76~6.80 (1H, m), 6.94~7.06 (3H, m), 7.25~7.35 (1H, m), 7.59 (1H, d, J=16 Hz), 7.81~7.92 (2H, m), 9.0~11.0 (1H, br).

EXAMPLE 6

Ethyl (E)-2-(3,4-dimethoxystyryl)benzimidazole-4-carboxylate

M.p. 116°–118° C. (ethyl acetate-n-hexane).

Elem. Anal. (C₂₀H₂₀N₂O₄). Calcd (%): C: 68.17 H: 5.72 N: 7.95. Found (%): C: 68.20 H: 5.60 N: 7.92.

IR (KBr) cm⁻¹: 3500~2600, 1705, 1275, 1140, 760.

NMR (CDCl₃) δ: 1.47 (3H, t, J=7 Hz), 3.92 (3H, s), 3.95 (3H, s), 4.48 (2H, q, J=7 Hz), 6.84~6.89 (1H, m), 7.04 (1H, d, J=16 Hz), 7.11~7.17 (2H, m), 7.25~7.33 (1H, m), 7.63 (1H, d, J=16 Hz), 7.85~7.95 (2H, m), 9.0~11.0 (1H, br).

EXAMPLE 7

Methyl (E)-2-(3,4-dimethoxy-alpha-methylstyryl)benzimidazole-4-carboxylate

M.p. 115°–117° C. (ethyl acetate-ether).

Elem. Anal. (C₂₀H₂₀N₂O₄). Calcd (%): C: 68.17 H: 5.72 N: 7.95. Found (%): C: 68.23 H: 5.57 N: 7.97.

IR (KBr) cm⁻¹: 3500~2600, 3460, 1700, 1275, 1145.

NMR (CDCl₃) δ: 2.52 (3H, d, J=2 Hz), 3.93 (6H, s), 4.02 (3H, s), 6.92 (1H, d, J=8 Hz), 7.01 (1H, s), 7.09 (1H, d, J=8 Hz), 7.28 (1H, t, J=8 Hz) 7.46 (1H, d, J=2 Hz), 7.87 (1H, dd, J=8 Hz, 1.5 Hz), 7.97 (1H, dd, J=8 Hz, 1.5 Hz), 10.42~10.50 (1H, br).

EXAMPLE 8

Methyl (E)-2-(3,4-dimethoxy-beta-methylstyryl)benzimidazole-4-carboxylate

M.p. 188°–190° C. (ethyl acetate).

Elem. Anal. (C₂₀H₂₀N₂O₄). Calcd (%): C: 68.17 H: 5.72 N: 7.95. Found (%): C: 68.25 H: 5.76 N: 7.94.

IR (KBr) cm⁻¹: 3500~2600, 3330, 1710, 1280, 1145, 760.

NMR (CDCl₃) δ: 2.79 (3H, d, J=2 Hz), 3.93 (3H, s), 3.96 (3H, s), 4.01 (3H, s), 6.75 (1H, d, J=2 Hz), 6.89 (1H, d, J=8 Hz), 7.10 (1H, d, J=1.5 Hz) 7.16 (1H, dd, J=8 Hz, 1.5 Hz), 7.29 (1H, t, J=8 Hz), 7.88 (1H, dd, J=8 Hz, 1.5 Hz), 7.98 (1H, dd, J=8 Hz, 1.5 Hz), 10.24~10.44 (1H, br).

EXAMPLE 9

Methyl 2-[2-(3,4-dimethoxyphenyl)ethynyl]benzimidazole-4-carboxylate

M.p. 200°–202° C. (chloroform-ethyl acetate).

Elem. Anal. (C₁₉H₁₆N₂O₄). Calcd (%): C: 67.85 H: 4.79 N: 8.33. Found: (%): C: 67.77 H: 4.67 N: 8.26.

IR (KBr) cm⁻¹: 3500~2600, 3340, 2230, 1720, 1270, 1140, 760.

NMR (CDCl₃) δ: 3.91 (3H, s), 3.92 (3H, s), 4.02 (3H, s), 6.84 (1H, d, J=8 Hz), 7.11 (1H, d, J=1.5 Hz), 7.22 (1H, dd, J=8 Hz, 1.5 Hz), 7.35 (1H, t, J=8 Hz), 7.94 (1H, dd, J=8 Hz, 1.5 Hz), 7.98 (1H, dd, J=8 Hz, 1.5 Hz), 12.5~13.8 (1H, br).

EXAMPLE 10

Methyl (E)-2-(4-hydroxy-3-methoxystyryl)benzimidazole-4-carboxylate

M.p. 176°–178° C. (ethyl acetate-ether).

Elem. Anal. (C₁₈H₁₆N₂O₄). Calcd (%): C: 66.66 H: 4.97 N: 8.64. Found: (%): C: 66.47 H: 4.79 N: 8.52.

IR (KBr) cm⁻¹: 3600~2400, 3450, 1700, 1285, 1145, 760.

NMR (CDCl₃) δ: 3.94 (3H, s), 4.02 (3H, s), 6.92 (1H, d, J=8 Hz), 7.02 (1H, d, J=16 Hz), 7.03~7.13 (4H, m), 7.28 (1H, t, J=8 Hz), 7.59 (1H, d, J=16 Hz), 7.85 (1H, dd, J=8 Hz, 1.5 Hz), 7.92 (1H, dd, J=8 Hz, 1.5 Hz).

EXAMPLE 11

Methyl (E)-2-(4-allyloxy-3-methoxystyryl)benzimidazole-4-carboxylate

M.p. 126°–128° C. (ethyl acetate-ether).

Elem. Anal. (C₂₁H₂₀N₂O₄). Calcd (%): C: 69.22 H: 5.53 N: 7.69. Found (%): C: 69.17 H: 5.53 N: 7.68.

IR (KBr) cm⁻¹: 3600~2500, 1720, 1275, 1140, 930, 755.

NMR (CDCl₃) δ: 3.93 (3H, s), 4.01 (3H, s), 4.65 (2H, dt, J=5 Hz, 1 Hz), 5.31 (1H, dd, J=10 Hz, 1 Hz), 5.42 (1H, dd, J=16 Hz, 1 Hz), 6.09 (1H, ddd, J=16 Hz, 10 Hz, 5 Hz), 6.88 (1H, d, J=8 Hz), 7.02 (1H, d, J=16 Hz), 7.09 (1H, dd, J=8 Hz, 1.5 Hz), 7.11 (1H, d, J=1.5 Hz), 7.28 (1H, t, J=8 Hz), 7.58 (1H, d, J=16 Hz), 7.86 (1H, dd, J=8 Hz, 1.5 Hz), 7.92 (1H, dd, J=8 Hz, 1.5 Hz), 10.7~9.7 (1H, br).

EXAMPLE 12

Methyl 2-[trans-2-(3,4-dimethoxyphenyl)cyclopropyl]-benzimidazole-4-carboxylate M.p. 156°–158° C. (ethyl acetate).

Elem. Anal. ($C_{20}H_{20}N_2O_4$). Calcd (%): C: 68.17 H: 5.72 N: 7.95. Found (%): C: 68.30 H: 5.70 N: 7.97.

IR (KBr) cm$^{-1}$: 3500~2600, 3340, 1710, 1270, 1145, 740.

NMR (CDCl$_3$) δ: 1.61 (1H, ddd, J=5.5 Hz, 6.5 Hz, 8.5 Hz), 1.93 (1H, dt, J=9 Hz, 5.5 Hz), 2.27 (1H, ddd, J=4.5 Hz, 5.5 Hz, 8.5 Hz), 2.73 (1H, ddd, J=4.5 Hz, 6.5 Hz, 9 Hz), 3.87 (6H, s), 3.99 (3H, s), 6.70 (1H, d, J=8 Hz), 6.72 (1H, d, J=1.5 Hz), 6.81 (1H, dd, J=8 Hz, 1.5 Hz), 7.26 (1H, t, J=8 Hz), 7.84 (1H, dd, J=8 Hz, 1.5 Hz), 7.88 (1H, dd, J=8 Hz, 1.5 Hz), 11.8~9.4 (1H, br).

EXAMPLE 13

Methyl 2-[cis-2-(3,4-dimethoxyphenyl)cyclopropyl]benzimidazole-4-carboxylate M.p. 132°–134° C. (ether).

Elem. Anal. ($C_{20}H_{20}N_2O_4$). Calcd (%): C: 68.17 H: 5.72 N: 7.95. Found (%): C: 68.52 H: 5.70 N: 8.03.

IR (KBr) cm$^{-1}$: 3500~2600, 3340, 1710, 1270, 1145, 745.

NMR (CDCl$_3$) δ: 1.71 (1H, dt, J=5 Hz, 8.5 Hz), 1.78 (1H, dt, J=5.5 Hz, 6.5 Hz), 2.71 (3H, dd, J=6.5 Hz, 8.5 Hz), 3.66 (3H, s), 3.79 (3H, s), 3.86 (3H, s), 6.74 (1H, d, J=8 Hz), 6.69 (1H, d, J=1.5 Hz), 6.85 (1H, dd, J=8 Hz, 1.5 Hz), 7.18 (1H, t, J=8 Hz), 7.74 (1H, dd, J=8 Hz, 1.5 Hz), 7.81 (1H, dd, J=8 Hz, 1.5 Hz), 9.6~0.2 (1H, br).

EXAMPLE 14

Methyl (E)-2-(4-methoxystyryl)benzimidazole-4-carboxylate

M.p. 137°–138° C. (ethyl acetate-ether).

Elem. Anal. ($C_{18}H_{16}N_2O_3$). Calcd (%): C: 70.12 H: 5.23 N: 9.09. Found (%): C: 69.84 H: 5.20 N: 9.01.

IR (KBr) cm$^{-1}$: 3500~2600, 1715, 1280, 1145.

NMR (CDCl$_3$) δ: 3.84 (3H, s), 4.01 (3H, s), 6.90 (2H, d, J=8 Hz), 6.98 (1H, d, J=16 Hz), 7.28 (1H, t, J=8 Hz), 7.48 (2H, d, J=8 Hz), 7.62 (1H, d, J=16 Hz), 7.85 (1H, dd, J=8 Hz, 1.5 Hz), 7.93 (1H, dd, J=8 Hz, 1.5 Hz), 9.99~10.60 (1H, br).

EXAMPLE 15

Methyl (E)-2-(3-methoxystyryl)benzimidazole-4-carboxylate

M.p. 145°–147° C. (ethyl acetate-ether).

Elem. Anal. ($C_{18}H_{16}N_2O_3$). Calcd (%): C: 70.12 H: 5.23 N: 9.09. Found (%): C: 70.39 H: 5.17 N: 9.11.

IR (KBr) cm$^{-1}$: 3500~2600, 1700, 1285, 1145.

NMR (CDCl$_3$) δ: 3.84 (3H, s), 4.02 (3H, s), 6.90 (1H, dd, J=8 Hz, 1.5 Hz), 7.22~7.60 (2H, m), 7.14 (1H, d, J=16 Hz), 7.30 (1H, t, J=8 Hz), 7.31 (1H, t, J=8 Hz), 7.63 (1H, d, J=16 Hz), 7.88 (1H, dd, J=8 Hz, 1.5 Hz), 7.94 (1H, dd, J=8 Hz, 1.5 Hz), 10.00~11.60 (1H, m).

EXAMPLE 16

Methyl (E)-2-(2-methoxystyryl)benzimidazole-4-carboxylate

M.p. 149°–151° C. (ethyl acetate-ether).

Elem. Anal. ($C_{18}H_{16}N_2O_3$). Calcd (%): C: 70.12 H: 5.23 N: 9.09. Found (%): C: 69.80 H: 5.17 N: 9.06.

IR (KBr) cm$^{-1}$: 3500~2600, 1730, 1710, 1280, 1150.

NMR (CDCl$_3$) δ: 3.87 (3H, s), 3.99 (3H, s), 6.89 (1H, d, J=8 Hz), 6.95 (1H, t, J=8 Hz), 7.22~7.36 (2H, m), 7.27 (1H, d, J=16 Hz), 7.35 (1H, d, J=8 Hz), 7.86 (1H, d, J=8 Hz), 7.90 (1H, d, J=16 Hz), 7.93 (1H, d, J=8 Hz), 9.50~10.8 (1H, br).

EXAMPLE 17

(E)-2-(3,4-Dimethoxystyryl)benzimidazole-4-carboxylic acid

Methyl (E)-2-(3,4-dimethoxystyryl)benzimidazole-4-carboxylate obtained in Example 1 (8.56 g) was dissolved in 90 ml ethanol, refluxed for 15 hours after addition of 10 ml water and 1.80 g potassium hydroxide, the reaction solution was concentrated in vacuo, water was added to the residue, acidified with acetic acid, the separating crystals were collected by filtration, air-dried, and recrystallized from ethanol to give 7.62 g of yellow crystals. M.p. 289°–291° C.

Elem. Anal. ($C_{18}H_{16}N_2O_4 \cdot 1/10H_2O$) Calcd (%): C: 66.29 H: 5.01 N: 8.59. Found (%): C: 66.18 H: 4.99 N: 8.52.

IR (KBr) cm$^{-1}$: 3500~1750, 3400, 1680, 1270, 1135, 755.

NMR (DMSO-d$_6$) δ: 3.80 (3H, s), 3.84 (3H, s), 7.01 (1H, d, J=8 Hz), 7.13~7.41 (4H, m), 7.70~7.88 (3H, m), 12.10~12.40 (1H, br), 12.90~13.40 (1H, br).

By the similar manner as Example 1, the following substances were obtained.

EXAMPLE 18

Methyl (E)-2-[4-methoxy-3-(2-pyridylmethoxy)styryl]-benzimidazole-4-carboxylate dihydrochloride Yellow powder, m.p. 232°–235° C. (decompn) (EtOH).

Elem. Anal. ($C_{24}H_{21}N_3O_4 \cdot 2HCl \cdot 0.4H_2O$). Calcd (%): C: 58.17 H: 4.84 N: 8.48 Cl: 14.31. Found (%): C: 58.32 H: 5.07 N: 8.38 Cl: 14.33.

IR (KBr) cm$^{-1}$: 3600~2500, 1720, 1300, 1140, 755.

NMR (DMSO-d$_6$) δ: 3.89 (3H, s), 4.03 (3H, s), 5.37 (2H, s), 7.02~7.77 (7H, m), 7.96~8.13 (3H, m), 8.19 (1H, d, 16 Hz), 8.70 (1H, d, 7 Hz).

EXAMPLE 19

Methyl (E)-2-[4-methoxy-3-(2-piperidinoethoxy)styryl]benzimidazole-4-carboxylate dihydrochloride Yellow powder, m.p. 136°–139° C. (EtOH, Et$_2$O).

Elem. Anal. ($C_{25}H_{29}N_3O_4 \cdot 2HCl \cdot 2.8H_2O$). Calcd (%): C: 53.73 H: 6.60 N: 7.52 Cl: 12.69. Found (%): C: 53.74 H: 6.67 N: 7.42 Cl: 12.71.

IR (KBr) cm$^{-1}$: 3600~2400, 1725, 1265, 1140, 755.

NMR (DMSO-d$_6$) δ: 1.64~1.92 (6H, m), 2.90~3.7 (6H, m), 3.88 (3H, s), 4.03 (3H, s), 4.51 (2H, m), 2.8~4.8 (broad), 7.18 (1H, d, 8 Hz), 7.32~7.50 (3H, m), 7.56 (1H, t, 8 Hz), 7.96~8.07 (2H, m), 8.16 (1H, d, 16 Hz), 10.4~10.7 (1H, broad (s)).

EXAMPLE 20

Methyl (E)-2-[4-methoxy-3-(2-pyridylmethoxy)styryl]benzimidazole-4-carboxylate Yellow crystals, m.p. 154°–156° C. (EtOAc).

Elem. Anal. ($C_{24}H_{21}N_3O_4 \cdot 0.1H_2O$). Calcd (%): C: 69.09 H: 5.12 N: 10.07. Found (%): C: 68.94 H: 5.09 N: 9.79.

IR (KBr) cm$^{-1}$: 3600~2500, 1720, 1260, 1130, 755.

NMR (CDCl$_3$) δ: 3.94 (3H, s), 4.02 (3H, s), 5.34 (2H, s), 6.92 (1H, d, 16 Hz), 6.91 (1H, d, 8 Hz), 7.10~7.34 (3H, m), 7.28 (1H, t, 8 Hz), 7.57 (1H, d, 16 Hz), 7.52~7.63 (1H, m), 7.70 (1H, td, 7 Hz, 1.5 Hz), 7.86 (1H, dd, 8 Hz, 1.5 Hz), 7.92 (1H, dd, 8 Hz, 1.5 Hz), 8.62 (1H, dd, 7 Hz, 1.5 Hz), 9.70~10.7 (1H, broad.).

EXAMPLE 21

Methyl (E)-2-(4-n-butoxystyryl)benzimidazole-4-carboxylate.

Yellow crystals, m.p. 117°–119° C. (AcOEt).

Elem. Anal. ($C_{21}H_{22}N_2O_3$). Calcd (%): C: 71.98 H: 6.33 N: 7.99. Found (%): C: 71.81 H: 6.41 N: 7.93.

IR (KBr) cm$^{-1}$: 3200, 1735, 1715, 1130.

NMR (CDCl$_3$) δ: 0.97 (3H, t, 7 Hz), 1.47 (2H, hexaplet, 7 Hz), 1.77 (2H, pentaplet, 7 Hz), 3.97 (2H, t, 7 Hz), 3.99 (3H, s), 6.87 (2H, d, 8 Hz), 6.97 (1H, d, 16 Hz), 7.27 (1H, t, 8 Hz), 7.44 (2H, d, 8 Hz), 7.60 (1H, d, 16 Hz), 7.84 (1H, dd, 8 Hz, 1.5 Hz), 7.91 (1H, dd, 8 Hz, 1.5 Hz), 9.62~11.32 (1H, m).

EXAMPLE 22

Methyl (E)-2-(3-chloro-4-methoxystyryl)benzimidazole-4-carboxylate phosphate

Yellow powder, m.p. 287°–289° C. (MeOH).

Elem. Anal. ($C_{18}H_{15}N_2ClO_3 \cdot H_3PO_4$). Calcd (%): C: 49.05 H: 4.12 N: 6.36. Found (%): C: 49.00 H: 4.03 N: 6.44.

IR (KBr) cm$^{-1}$: 3600~2100, 1735, 1270, 1085, 750.

NMR (DMSO-d$_6$) δ: 3.91 (3H, s), 3.97 (3H, s), 7.20~7.39 (3H, m), 7.57~7.92 (5H, m), 12.29 (1H, broad. s), 8.0~13.0 (broad).

EXAMPLE 23

Methyl (E)-2-(3-chloro-4-methoxystyryl)benzimidazole-4-carboxylate

Pale yellow crystals, m.p. 138°–140° C. (EtOAc-Et$_2$O).

Elem. Anal. ($C_{18}H_{15}N_2ClO_3$). Calcd (%): C: 63.07 H: 4.41 N: 8.17 Found (%): C: 63.23 H: 4.29 N: 8.17.

IR (KBr) cm$^{-1}$: 3500~2600, 1710, 1265, 1140, 745.

NMR (CDCl$_3$) δ: 3.95 (3H, s), 4.04 (3H, s), 6.94 (1H, d, 8 Hz), 7.01 (1H, d, 16 Hz), 7.30 (1H, t, 8 Hz), 7.41 (1H, dd, 8 Hz, 1.5 Hz), 7.58 (1H, d, 16 Hz), 7.60 (1H, d, 1.5 Hz), 7.88 (1H, dd, 8 Hz, 1.5 Hz), 7.94 (1H, dd, 8 Hz, 1.5 Hz).

EXAMPLE 24

Methyl (E)-2-[4-(2-acetyloxyethoxy)styryl]benzimidazole-4-carboxylate phosphate

Yellow crystals, m.p. 265°–267° C.

Elem. Anal. ($C_{21}H_{20}N_2O_5 \cdot H_3PO_4 \cdot 0.2H_2O$). Calcd (%): C: 52.33 H: 4.89 N: 5.81. Found (%): C: 52.17 H: 4.90 N: 5.81.

IR (KBr) cm$^{-1}$: 3300~2330, 1730, 1240, 1180, 1080.

NMR (DMSO-d$_6$) δ: 2.07 (3H, s), 3.99 (3H, s), 4.25 (2H, t, 7 Hz), 4.37 (2H, t, 7 Hz), 7.06 (2H, d, 8 Hz), 7.27 (1H, d, 16 Hz), 7.30 (1H, t, 8 Hz), 7.63 (2H, d, 8 Hz), 7.80 (1H, d, 8 Hz), 7.84 (1H, d, 16 Hz), 7.88 (1H, d, 8 Hz), 12.16~12.37 (1H, m).

EXAMPLE 25

Methyl (E)-2-[4-(2-acetyloxyethoxy)styryl]benzimidazole-4-carboxylate

Pale yellow crystals, m.p. 130°–131° C. (AcOEt-Et$_2$O).

Elem. Anal. ($C_{21}H_{20}N_2O_5 \cdot \frac{1}{2}H_2O$). Calcd (%): C: 64.77 H: 5.44 N: 7.19. Found (%): C: 64.91 H: 5.26 N: 7.37.

IR (KBr) cm$^{-1}$: 3330, 1725, 1710, 1280, 1140.

NMR (CDCl$_3$) δ: 2.11 (3H, s), 4.02 (3H, s), 4.20 (2H, t, 7 Hz), 4.44 (2H, t, 7 Hz), 6.93 (2H, d, 8 Hz), 7.02 (1H, d, 16 Hz), 7.28 (1H, t, 8 Hz), 7.50 (2H, d, 8 Hz), 7.62 (1H, d, 16 Hz), 7.86 (1H, dd, 8 Hz, 1.5 Hz), 7.93 (1H, dd, 8 Hz, 1.5 Hz), 9.82~10.54 (1H, m).

EXAMPLE 26

Methyl (E)-2-(2,4,6-trimethoxystyryl)benzimidazole-4-carboxylate phosphate

Yellow powder, m.p. 246°–249° C. (MeOH).

Elem. Anal. ($C_{20}H_{20}N_2O_5 \cdot H_3PO_4 \cdot 0.85H_2O$). Calcd (%): C: 49.87 H: 5.17 N: 5.82. Found (%): C: 49.83 H: 5.22 N: 5.90.

IR (KBr) cm$^{-1}$: 3600~2200, 1720, 1300, 1115, 750.

NMR (DMSO-d$_6$) δ: 3.85 (3H, s), 3.93 (6H, s), 3.97 (3H, s), 6.32 (2H, s), 7.25 (1H, t, 8 Hz), 7.61 (1H, d, 16 Hz), 7.73 (1H, dd, 8 Hz, 1.5 Hz), 7.83 (1H, dd, 8 Hz, 1.5 Hz), 8.12 (1H, d, 16 Hz), 11.8~12.8 (1H, broad.).

EXAMPLE 27

Methyl (E)-2-(2,3,4-trimethoxystyryl)benzimidazole-4-carboxylate phosphate

Yellow powder, mp. 252°–254° C. (MeOH).

Elem. Anal. ($C_{20}H_{20}N_2O_5 \cdot H_3PO_4$). Calcd (%): C: 51.51 H: 4.97 N: 6.01. Found (%): C: 51.21 H: 5.02 N: 5.98.

IR (KBr) cm$^{-1}$: 3600~2200, 1735, 1300, 1100, 750.

NMR (DMSO-d$_6$) δ: 3.80 (3H, s), 3.86 (3H, s), 3.89 (3H, s), 3.98 (3H, s), 6.93 (1H, d, 8 Hz), 7.29 (1H, t, 8 Hz), 7.37 (1H, d, 16 Hz), 7.41 (1H, d, 8 Hz), 7.78 (1H, dd, 8 Hz, 1.5 Hz), 7.88 (1H, dd, 8 Hz, 1.5 Hz), 7.93 (1H, d, 16 Hz), 11.9~12.8 (1H, broad.).

EXAMPLE 28

Methyl (E)-2-(2,3,4-trimethoxystyryl)benzimidazole-4-carboxylate

Yellow crystals, m.p. 96°–109° C.

Elem. Anal. ($C_{20}H_{20}N_2O_5 \cdot 0.8MeOH$). Calcd (%): C: 63.41 H: 5.93 N: 7.11. Found (%): C: 63.30 H: 5.97 N: 7.23.

IR (KBr) cm$^{-1}$: 3600~2700, 1720, 1290, 755 NMR (CDCl$_3$) δ: 3.90 (H, s), 3.97 (3H, s), 4.02 (3H, s), 6.72 (1H, d, 8 Hz), 7.18 (1H, d, 16 Hz), 7.28 (1H, t, 8 Hz), 7.32 (1H, d, 8 Hz), 7.78 (1H, d, 16 Hz), 7.87 (1H, dd, 8 Hz, 1.5 Hz), 7.94 (1H, dd, 7 Hz, 1.5 Hz), 9.9~11.2 (1H, broad.).

EXAMPLE 29

Methyl (E)-2-(4-n-propyloxystyryl)benzimidazole-4-carboxylate phosphate

Yellow crystals, m.p. 273°–274° C.

Elem. Anal. ($C_{20}H_{20}N_2O_3 \cdot H_3PO_4 \cdot \frac{1}{2}H_2O$), Calcd (%): C: 54.18 H: 5.46 N: 6.32, Found (%): C: 54.16 H: 5.32 N: 6.52, IR (KBr) cm$^{-1}$: 3300~2330, 1740, 1270, 1180, 1080, NMR (DMSO-d$_6$) δ: 0.99 (3H, t, 7 Hz), 1.76 (2H, pentaplet, 7 Hz), 3.98 (3H, s), 3.99 (2H, t,), 7.01 (2H, d, 8 Hz), 7.24 (1H, d, 16 Hz), 7.29 (1H, t, 8 Hz), 7.59 (2H, d, 8 Hz), 7.78 (1H, d, 8 Hz), 7.82 (1H, d, 16 Hz), 7.88 (1H, d, 8 Hz), 12.07~12.42 (1H, m).

EXAMPLE 30

Methyl (E)-2-[4-(2-propynyloxy)styryl]benzimidazole-4-carboxylate phosphate

Yellow crystals, m.p. 288°–290° C.

Elem. Anal. ($C_{20}H_{18}N_2O_3 \cdot H_3PO_4$). Calcd (%): C: 55.82 H: 4.45 N: 6.51. Found (%): C: 55.72 H: 4.40 N: 6.52.

IR (KBr) cm$^{-1}$: 3300~2330, 1730, 1250, 1180, 1090.

NMR (DMSO-d$_6$) δ: 3.59 (1H, t, 2 Hz), 3.98 (3H, s), 4.86 (2H, d, 2 Hz), 7.07 (2H, d, 8 Hz), 7.27 (1H, d, 16 Hz), 7.29 (1H, t, 8 Hz), 7.62 (2H, d, 8 Hz), 7.78 (1H, dd, 8 Hz, 1.5 Hz), 7.84 (1H, d, 16 Hz), 7.86 (1H, dd, 8 Hz, 1.5 Hz), 12.12~12.48 (1H, m).

EXAMPLE 31

Methyl (E)-2-(4-n-propyloxystyryl)benzimidazole-4-carboxylate

Yellow crystals, m.p. 108°–110° C.

Elem. Anal. ($C_{20}H_{20}N_2O_3$). Calcd (%): C: 71.41 H: 5.99 N: 8.33, Found (%): C: 71.41 H: 5.90 N: 8.21, IR (KBr) cm$^{-1}$: 3500~2600, 1730, 1710, 1700, 1260, 1140.

NMR (CDCl$_3$) δ: 1.03 (3H, t, 7 Hz), 1.82 (2H, hexaplet, 7 Hz), 3.96 (2H, t, 7 Hz), 4.00 (3H, s), 6.89 (2H, d, 8 Hz), 6.98 (1H, d, 16 Hz), 7.27 (1H, t, 8 Hz), 7.48 (2H, d, 8 Hz), 7.60 (1H, d, 16 Hz), 7.85 (1H, d, 8 Hz), 7.92 (1H, d, 8 Hz), 9.87~10.76 (1H, m).

EXAMPLE 32

Methyl (E)-2-(4-allyloxystyryl)benzimidazole-4-carboxylate phosphate

Yellow crystals, m.p. 261°–263° C.

Elem. Anal. ($C_{20}H_{18}N_2O_3 \cdot H_3PO_4$). Calcd (%): C: 55.56 H: 4.90 N: 6.58, Found (%): C: 55.53 H: 4.86 N: 6.59, IR (KBr) cm$^{-1}$: 3300~2330, 1740, 1260, 1085.

NMR (DMSO-d$_6$) δ: 3.97 (3H, s), 4.63 (2H, d, 6 Hz), 5.28 (1H, dd, 10 Hz, 1.5 Hz cis-configuration), 5.42 (1H, dd, 16 Hz, 1.5 Hz, trans-configuration), 5.96~6.20 (1H, m), 7.03 (2H, d, 8 Hz), 7.26 (1H, d, 16 Hz), 7.28 (1H, t, 8 Hz), 7.60 (2H, d, 8 Hz), 7.78 (1H, dd, 8 Hz, 1.5 Hz), 7.82 (1H, d, 16 Hz), 7.85 (1H, dd, 8 Hz, 1.5 Hz), 12.00~12.58 (1H, m).

EXAMPLE 33

Methyl (E)-2-[4-(2-propynyloxy)styryl]benzimidazole-4-carboxylate

Yellow crystals, m.p. 138°–140° C. (AcOEt).

Elem. Anal. ($C_{20}H_{16}N_2O_3$), Calcd (%): C: 72.28 H: 4.85 N: 8.43. Found (%): C: 72.31 H: 4.65 N: 8.42.

IR (KBr) cm$^{-1}$: 3440, 3260, 1695, 1175.

NMR (CDCl$_3$) δ: 2.55 (1H, t, 2 Hz), 4.02 (3H, s), 4.73 (2H, s), 7.02 (2H, d, 8 Hz), 7.03 (1H, d, 16 Hz), 7.09 (1H, t, 8 Hz), 7.52 (2H, d, 8 Hz), 7.62 (1H, d, 16 Hz), 7.87 (1H, d, 8 Hz), 7.94 (1H, d, 8 Hz), 10.00~10.62 (1H, m).

EXAMPLE 34

Methyl (E)-2-(4-methylsulfinylstryryl)benzimidazole-4-carboxylate

Yellow crystals, m.p. 226°–228° C. (EtOH).

Elem. Anal. ($C_{18}H_{16}N_2O_3S$). Calcd (%): C: 63.51 H: 4.74 N: 8.23. Found (%): C: 63.50 H: 4.65 N: 8.17.

IR (KBr) cm$^{-1}$: 3240, 1720, 1280, 1035,

NMR (CDCl$_3$) δ: 2.77 (3H, s), 4.03 (3H, s), 7.25 (1H, d, 16 Hz), 7.32 (1H, t, 8 Hz), 7.70 (4H, s), 7.73 (1H, d, 16 Hz), 7.92 (1H, dd, 8 Hz, 1.5 Hz), 7.96 (1H, dd, 8 Hz, 1.5 Hz), 9.92~10.84 (1H, m).

EXAMPLE 35

Methyl (E)-2-(4-allyloxystyryl)benzimidazole-4-carboxylate

Yellow crystals, m.p. 100°–102° C. (Et$_2$O).

Elem. Anal. ($C_{20}H_{18}N_2O_3$). Calcd (%): C: 71.84 H: 5.43 N: 8.38. Found (%): C: 71.80 H: 5.32 N: 8.48.

IR (KBr) cm$^{-1}$: 3600~2800, 1725, 1270, 1140.

NMR (CDCl$_3$) δ: 3.99 (3H, s), 4.54 (2H, d-like, 6 Hz), 5.28 (1H, dd, 10 Hz 1.5 Hz cis-configuration), 5.40 (1H, dd, 16 Hz trans-configuration), 5.94~6.15 (1H, m), 6.89 (2H, d, 8 Hz), 6.97 (1H, d, 16 Hz), 7.26 (1H, t, 8 Hz), 7.46 (2H, d, 8 Hz), 7.59 (1H, d, 16 Hz), 7.84 (1H, dd, 8 Hz, 1.5 Hz), 7.90 (1H, dd, 8 Hz, 1.5 Hz), 10.14~10.68 (1H, m).

EXAMPLE 36

Methyl (E)-2-[4-(2-methoxyethoxy)styryl]benzimidazole-4-carboxylate phosphate

Yellow crystals, m.p. 263°–265° C.

Elem. Anal. ($C_{20}H_{20}N_2O_4 \cdot H_3PO_4$). Calcd (%): C: 53.34 H: 5.15 N: 6.22. Found (%): C: 53.19 H: 5.23 N: 6.25.

IR (KBr) cm$^{-1}$: 3300~2330, 1740, 1270, 1085.

NMR (DMSO-d$_6$) δ: 3.32 (3H, s), 3.67 (2H, t, 6 Hz), 3.97 (3H, s), 4.15 (2H, t, 6 Hz), 7.03 (2H, d, 8 Hz), 7.24 (1H, d, 16 Hz), 7.29 (1H, t, 8 Hz), 7.60 (2H, d, 8 Hz), 7.78 (1H, d, 8 Hz), 7.83 (1H, d, 16 Hz), 7.86 (1H, d, 8 Hz), 11.60~12.80 (1H, m).

EXAMPLE 37

Methyl (E)-2-[4-(2-methoxyethoxy)styryl]benzimidazole-4-carboxylate

Yellow crystals, m.p. 127°–128° C.

Elem. Anal. ($C_{20}H_{20}N_2O_4$). Calcd. (%): C: 68.17 H: 5.72 N: 7.95. Found (%): C: 68.29 H: 5.73 N: 7.95.

IR (KBr) cm$^{-1}$: 3300, 1730, 1710, 1280, 1180, 1135.

NMR (CDCl$_3$) δ: 3.45 (3H, s), 3.75 (2H, t, 8 Hz), 3.99 (3H, s), 4.13 (2H, t, 8 Hz), 6.91 (2H, d, 8 Hz), 6.97 (1H, d, 16 Hz), 7.26 (1H, t, 8 Hz), 7.46 (2H, d, 8 Hz), 7.60 (1H, d, 16 Hz), 7.84 (1H, dd, 8 Hz, 1.5 Hz), 7.92 (1H, dd, 8 Hz, 1.5 Hz), 9.90~10.72 (1H, m).

EXAMPLE 38

Methyl (E)-2-(4-n-butoxystyryl)benzimidazole-4-carboxylate phosphate

Yellow crystals, m.p. 266°–268° C.

Elem. Anal. (C$_{21}$H$_{22}$N$_2$O$_3$·H$_3$PO$_4$). Calcd (%): C: 56.25 H: 5.62 N: 6.25. Found (%): C: 56.23 H: 5.61 N: 6.36.

IR (KBr) cm$^{-1}$: 3000~2330, 1740, 1250, 1080.

NMR (DMSO-d$_6$) δ: 0.94 (3H, t, 8 Hz), 1.34~1.54 (2H, m), 1.64~1.80 (2H, m), 3.97 (3H, s), 4.03 (2H, t, 8 Hz), 7.01 (2H, d, 8 Hz), 7.24 (1H, d, 16 Hz), 7.28 (1H, t, 8 Hz), 7.59 (2H, d, 8 Hz), 7.77 (1H, d, 8 Hz), 7.82 (1H, d, 16 Hz), 7.86 (1H, d, 8 Hz), 12.18~12.34 (1H, m).

EXAMPLE 39

Methyl (E)-2-[3-methoxy-4-(2-piperidinoethoxy)styryl]-benzimidazole-4-carboxylate dihydrochloride Yellow powder, m.p. 152°–156° C. (decompn.) (EtOH).

Elem. Anal. (C$_{25}$H$_{29}$N$_3$O$_4$·2HCl·1.7 H$_2$O). Calcd (%): C: 55.70 H: 6.43 N: 7.79 Cl: 13.15. Found (%): C: 55.52 H: 6.68 N: 7.85 Cl: 13.11.

IR (KBr) cm$^{-1}$: 3600~2300, 1725, 1265, 1140, 755.

NMR (DMSO-d$_6$) δ: 1.60~1.90 (6H, m), 2.8~4.1 (broad.) 3.90 (3H, s), 4.02 (3H, s), 4.50 (2H, t, 7 Hz), 7.18 (1H, d, 8 Hz), 7.22~7.36 (2H, m), 7.44 (1H, d, 16 Hz), 7.56 (1H, t, 8 Hz), 7.95~8.06 (1H, d, 16 Hz), 10.2~10.6 (1H, broad.).

EXAMPLE 40

Methyl (E)-2-(4-benzyloxystyryl)benzimidazole-4-carboxylate phosphate

Yellow crystals, m.p. 267°–268° C.

Elem. Anal. (C$_{24}$H$_{20}$N$_2$O$_3$·H$_3$PO$_4$). Calcd (%): C: 59.75 H: 4.81 N: 5.81. Found (%): C: 59.54 H: 4.80 N: 5.83.

IR (KBr) cm$^{-1}$: 3300~2330, 1725, 1250, 1080.

NMR (DMSO-d$_6$) δ: 3.97 (3H, s), 5.17 (2H, s), 7.09 (2H, d, 8 Hz), 7.18~7.52 (7H, m), 7.62 (2H, d, 8 Hz), 7.78 (1H, d, 8 Hz), 7.82 (1H, d, 16 Hz), 7.86 (1H, d, 8 Hz), 11.90~12.90 (1H, m).

EXAMPLE 41

Methyl (E)-2-(4-ethoxystyryl)benzimidazole-4-carboxylate phosphate

Yellow crystals, m.p. 276°–278° C.

Elem. Anal. (C$_{19}$H$_{18}$N$_2$O$_3$·H$_3$PO$_4$) Calcd (%): C: 54.29 H: 5.04 N: 6.66. Found (%): C: 54.08 H: 5.08 N: 6.69.

IR (KBr) cm$^{-1}$: 3300~2330, 1735, 1270, 1090.

NMR (DMSO-d$_6$) δ: 1.35 (3H, t, 8 Hz), 3.98 (3H, s), 4.09 (2H, q, 8 Hz), 7.00 (2H, d, 8 Hz), 7.24 (1H, d, 16 Hz), 7.28 (1H, t, 8 Hz), 7.60 (2H, d, 8 Hz), 7.78 (1H, d, 8 Hz), 7.82 (1H, d, 16 Hz), 7.86 (1H, d, 8 Hz), 12.18~12.44 (1H, m).

EXAMPLE 42

Methyl (E)-2-(4-benzyloxystyryl)benzimidazole-4-carboxylate

Yellow crystals, m.p. 145°–147° C. (AcOEt).

Elem. Anal. (C$_{24}$H$_{20}$N$_2$O$_3$). Calcd (%): C: 74.98 H: 5.24 N: 7.29. Found (%): C: 75.03 H: 5.04 N: 7.32.

IR (KBr) cm$^{-1}$: 3440, 1710, 1290, 1150.

NMR (CDCl$_3$) δ: 3.99 (3H, s), 5.08 (2H, s), 6.96 (2H, d, 8 Hz), 6.98 (1H, d, 16 Hz), 7.27 (1H, t, 8 Hz), 7.33~7.54 (7H, m), 7.60 (1H, d, 16 Hz), 7.85 (1H, dd, 8 Hz, 1.5 Hz), 7.92 (1H, dd, 8 Hz, 1.5 Hz), 9.96~10.53 (1H, m).

EXAMPLE 43

Methyl (E)-2-(4-ethoxystyryl)benzimidazole-4-carboxylate

Yellow crystals, m.p. 132°–134° C. (EtOH).

Elem. Anal. (C$_{19}$H$_{18}$N$_2$O$_3$). Calcd (%): C: 70.79 H: 5.63 N: 8.69. Found (%): C: 70.90 H: 5.54 N: 8.75.

IR (KBr) cm$^{-1}$: 3500~2600, 1730, 1280, 1180.

NMR (CDCl$_3$) δ: 1.44 (3H, t, 7 Hz), 4.03 (3H, s), 4.07 (2H, q, 7 Hz), 6.91 (2H, d, 8 Hz), 7.00 (1H, d, 16 Hz), 7.29 (1H, t, 8 Hz), 7.51 (2H, d, 8 Hz), 7.64 (1H, d, 8 Hz), 7.86 (1H, dd, 8,1.5 Hz), 7.92 (1H, dd, 8,1.5 Hz), 9.79~10.72 (1H, m).

EXAMPLE 44

Methyl (E)-2-(4-methoxy-3-methylstyryl)benzimidazole-4-carboxylate phosphate

Yellow powder, m.p. 288°–290° C. (MeOH).

Elem. Anal. (C$_{19}$H$_{18}$N$_2$O$_3$·H$_3$PO$_4$). Calcd (%): C: 54.29 H: 5.04 N: 6.66 P: 7.37. Found (%): C: 54.01 H: 5.04 N: 6.49 P: 7.25.

IR (KBr) cm$^{-1}$: 3500~2200, 1730, 1260, 1135, 750.

NMR (DMSO-d$_6$) δ: 2.21 (3H, s), 3.85 (3H, s), 3.98 (3H, s), 3.6~6.8 (broad. disappeared by D$_2$O), 7.02 (1H, d, 8 Hz), 7.25 (1H, d, 16 Hz), 7.29 (1H, t, 8 Hz), 7.43~7.54 (2H, m), 7.72~7.90 (3H, m), 11.8~12.5 (1H, broad. disappeared by D$_2$O).

EXAMPLE 45

Methyl (E)-2-(4-methoxy-3-methoxystyryl)benzimidazole-4-carboxylate

Yellow crystals, m.p. 166°–168° C. (EtOAc-Et$_2$O).

Elem. Anal. (C$_{19}$H$_{18}$N$_2$O$_3$). Calcd (%): C: 70.79 H: 5.63 N: 8.69. Found (%): C: 70.94 H: 5.58 N: 8.52.

IR (KBr) cm$^{-1}$: 3600~2500, 1720, 1285, 1130, 750.

NMR (CDCl$_3$) δ: 2.23 (3H, s), 3.85 (3H, s), 4.00 (3H, s), 6.80 (1H, d, 8 Hz), 6.98 (1H, d, 16 Hz), 7.25~7.39 (2H, m), 7.27 (1H, t, 8 Hz), 7.58 (1H, d, 16 Hz), 7.85 (1H, dd, 8 Hz, 1.5 Hz), 7.92 (1H, dd, 8 Hz, 1.5 Hz), 9.8~10.7 (1H, broad.).

EXAMPLE 46

Methyl (E)-2-[3-methoxy-4-(2-piperidinoethoxy)styryl]-benzimidazole-4-carboxylate Pale yellow crystals, m.p. 124°–126° C. (EtOAc-Et$_2$O).

Elem. Anal. (C$_{25}$H$_{29}$N$_3$O$_4$). Calcd (%): C: 68.95 H: 6.71 N: 9.65. Found (%): C: 69.06 H: 6.78 N: 9.70.

IR (KBr) cm$^{-1}$: 3600~2700, 1720, 1265, 1135, 755.

NMR (CDCl$_3$) δ: 1.35~1.69 (6H, m), 2.46~2.59 (4H, m), 2.82 (2H, t, 7 Hz), 3.89 (3H, s), 4.00 (3H, s), 4.19 (2H, t, 7 Hz), 6.89 (1H, d, 8 Hz), 7.01 (1H, d, 16 Hz), 7.04~7.14 (2H, m), 7.28 (1H, t, 8 Hz), 7.58 (1H, d, 16 Hz), 7.86 (1H, dd, 8 Hz, 1.5 Hz), 7.93 (1H, dd, 8 Hz, 1.5 Hz), 10.52 (1H, broad.singlet).

EXAMPLE 47

Methyl (E)-2-(3-benzyloxy-4-methoxystyryl)benzimidazole-4-carboxylate

Pale yellow crystal, m.p. 183°–185° C. (MeOH).

Elem. Anal. (C$_{23}$H$_{22}$N$_2$O$_4$). Calcd (%): C: 72.45 H: 5.35 N: 6.76. Found (%): C: 72.46 H: 5.41 N: 6.70.

IR (KBr) cm$^{-1}$: 3500~2600, 1730, 1265, 1130.

NMR (CDCl$_3$) δ: 3.91 (3H, s), 4.00 (3H, s), 5.18 (2H, s), 6.89 (1H, d, 8 Hz), 6.93 (1H, d, 16 Hz), 7.10 (2H, s like), 7.27 (1H, t, 8 Hz), 7.22~7.52 (5H, m), 7.54 (1H, d, 16 Hz), 7.85 (1H, dd, 8 Hz, 1.5 Hz), 7.92 (1H, dd, 8 Hz, 1.5 Hz), 10.02~10.66 (1H, m).

EXAMPLE 48

Methyl (E)-2-(4-methylthiostyryl)benzimidazole-4-carboxylate phosphate.

Yellow crystals, mp. 270°–271° C.

Elem. Anal. (C$_{18}$H$_{16}$N$_2$O$_2$S.H$_3$PO$_4$) Calcd (%): C: 51.18 H: 4.53 N: 6.63. Found (%): C: 51.03 H: 4.57 N: 6.56.

IR (KBr) cm$^{-1}$: 3200~2340, 1730, 1185, 1080.

NMR (DMSO-d$_6$) δ: 2.53 (3H, s), 3.98 (3H, s), 7.31 (1H, t, 8 Hz), 7.32 (2H, d, 8 Hz), 7.34 (1H, d, 16 Hz), 7.60 (2H, d, 8 Hz), 7.78 (1H, dd, 8 Hz, 1.5 Hz), 7.82 (1H, d, 16 Hz), 7.86 (1H, dd, 8 Hz, 1.5 Hz), 11.79~12.62 (1H, m).

EXAMPLE 49

Methyl (E)-2-(3-difluoromethoxy-4-methoxystyryl)benzimidazole-4-carboxylate

Yellow crystals, m.p. 140°–142° C. (EtOH).

Elem. Anal. (C$_{19}$H$_{16}$F$_2$N$_2$O$_4$). Calcd (%): C: 60.96 H: 4.31 N: 7.48 F: 10.15. Found (%): C: 61.27 H: 4.14 N: 7.41 F: 10.36.

IR (KBr) cm$^{-1}$: 3420~1690, 1280, 1145, 745.

NMR (CDCl$_3$) δ: 3.90 (3H, s), 4.00 (3H, s), 6.57 (1H, t, 75 Hz), 6.94 (1H, d, 8 Hz), 6.99 (1H, d, 16 Hz), 7.23~7.39 (3H, m), 7.57 (1H, d, 16 Hz), 7.86 (1H, dd, 8 Hz, 1.5 Hz), 7.92 (1H, dd, 8 Hz, 1.5 Hz), 9.80~10.7 (1H, broad.).

EXAMPLE 50

Methyl (E)-2-(4-difluoromethoxy-3-methoxystyryl)benzimidazole-4-carboxylate phosphate.

Yellow powder, m.p. 281°–285° C. (decompn.) (EtOH).

Elem. Anal. (C$_{19}$H$_{16}$F$_2$N$_2$O$_4$.H$_3$PO$_4$.0.2H$_2$O). Calcd (%) C: 58.98 H: 4.53 N: 7.24 F: 7.98 P: 6.51. Found (%) C: 58.93 H: 4.42 N: 7.29 F: 7.91 P: 6.48.

IR (KBr) cm$^{-1}$: 3500~2100, 1735, 1270, 750.

NMR (DMSO-d$_6$) δ: 3.93 (3H, s), 3.98 (3H, s), 4.2~5.8 (broad.), 7.11 (1H, t, 75 Hz), 7.22~7.52 (6H, m), 7.76~7.93 (3H, m), 11.9~12.8 (1H, broad.).

EXAMPLE 51

Methyl (E)-2-(4-difluoromethoxy-3-methoxystyryl)benzimidazole-4-carboxylate

Pale yellow crystals, mp. 96°–109° C.(EtOH).

Elem. Anal. (C$_{19}$H$_{16}$F$_2$N$_2$O$_4$.0.7H$_2$O). Calcd (%): C: 58.98 H: 4.53 N: 7.24. Found (%): C: 58.93 H: 4.42 N: 7.29.

IR (KBr) cm$^{-1}$: 3500~2800, 1705, 1270, 1140, 745.

NMR (CDCl$_3$) δ: 3.92 (3H, s), 4.02 (3H, s), 6.58 (1H, t, 75 Hz), 7.04~7.22 (4H, m), 7.30 (1H, t, 8 Hz), 7.60 (1H, d, 16 Hz), 7.88 (1H, dd, 8 Hz, 1.5 Hz), 7.94 (1H, dd, 8 Hz, 1.5 Hz), 10.7~10.2 (1H, broad.).

EXAMPLE 52

Methyl (E)-2-(4-methylthiostyryl)-benzimidazole-4-carboxylate

Yellow crystals, m.p. 135°–137° C. (AcOEt-Et$_2$O).

Elem. Anal. (C$_{19}$H$_{16}$N$_2$O$_2$S). Calcd (%): C: 66.65 H: 4.97 N: 8.64. Found (%): C: 66.68 H: 5.01 N: 8.50.

IR (KBr) cm$^{-1}$: 3300, 1725, 1710, 1690, 1270, 1140.

NMR (CDCl$_3$) δ: 2.49 (3H, s), 3.99 (3H, s), 7.07 (1H, d, 16 Hz), 7.19 (2H, d, 8 Hz), 7.27 (1H, t, 8 Hz), 7.42 (2H, d, 8 Hz), 7.61 (1H, d, 16 Hz), 7.85 (1H, dd, 8 Hz, 1.5 Hz), 7.92 (1H, dd, 8 Hz, 1.5 Hz), 8.00~9.64 (1H, m).

EXAMPLE 53

Methyl (E)-2-(4-ethoxy-3-methoxystyryl)benzimidazole-4-carboxylate phosphate

Yellow crystals, m.p. 278°–281° C. (MeOH).

Elem. Anal. (C$_{20}$H$_{20}$N$_2$O$_4$.H$_3$PO$_4$). Calcd (%): C: 53.34 H: 5.15 N: 6.22. Found (%): C: 53.14 H: 5.17 N: 6.24.

IR (KBr) cm$^{-1}$: 3300~2330, 1740, 1260, 1140.

NMR (DMSO-d$_6$) δ: 1.35 (3H, t, 6 Hz), 3.85 (3H, s), 3.97 (3H, s), 4.06 (2H, q, 6 Hz), 7.00 (1H, d, 8 Hz), 7.18 (1H, dd, 8 Hz, 1.5 Hz), 7.22~7.35 (3H, m), 7.78 (1H, d, 8 Hz), 7.80 (1H, d, 16 Hz), 7.84 (1H, d, 8 Hz), 12.16~12.38 (1H, m).

EXAMPLE 54

Methyl (E)-2-(4-methoxystyryl)benzimidazole-4-carboxylate phosphate

Yellow crystals, m.p. 271°–272° C. (decompn).

Elem. Anal. (C$_{18}$H$_{16}$N$_2$O$_3$.H$_3$PO$_4$). Calcd (%): C: 53.21 H: 4.71 N: 6.89. Found (%): C: 53.08 H: 4.66 N: 6.99.

IR (KBr) cm$^{-1}$: 3500~2000, 1735, 1275.

NMR (DMSO-d$_6$) δ: 3.81 (3H, s), 3.97 (3H, s), 7.02 (2H, d, 8 Hz), 7.25 (1H, d, 16 Hz), 7.28 (1H, t, 8 Hz), 7.61 (2H, d, 8 Hz), 7.78 (1H, d, 8 Hz), 7.83 (1H, d, 16 Hz), 7.85 (1H, d, 8 Hz), 12.25~12.33 (1H, broad. m, disappeared by D$_2$O).

EXAMPLE 55

Methyl (E)-2-[4-(2-acetyloxy)ethoxy-3-methoxystyryl]-benzimidazole-4-carboxylate Pale yellow crystals, mp. 133°–135° C. (AcOEt-Et$_2$O).

Elem. Anal. (C$_{22}$H$_{22}$N$_2$O$_6$). Calcd (%): C: 64.38 H: 5.40 N: 6.83. Found (%): C: 64.19 H: 5.52 N: 6.63.

IR (KBr) cm$^{-1}$: 3500~2400, 1730, 1275, 1140.

NMR (CDCl$_3$) δ: 2.11 (3H, s), 3.92 (3H, s), 4.02 (3H, s), 4.26 (2H, t, 6 Hz), 4.46 (2H, t, 6 Hz), 6.92 (1H, d, 8 Hz), 7.03 (1H, d, 16 Hz), 7.10 (1H, d, 8 Hz), 7.60 (1H, d, 16 Hz), 7.87 (1H, dd, 8 Hz, 1.5 Hz), 7.93 (1H, dd, 8 Hz, 1.5 Hz), 9.90~10.77 (1H, m).

EXAMPLE 56

Methyl (E)-2-(3-allyloxy-4-methoxystyryl)benzimidazole-4-carboxylate

Pale yellow crystals, m.p. 106°–107° C. (AcOEt-Et$_2$O).

Elem. Anal. (C$_{21}$H$_{20}$N$_2$O$_4$). Calcd (%): C: 69.13 H: 5.69 N: 7.53. Found (%): C: 69.09 H: 5.56 N: 7.60.

IR (KBr) cm$^{-1}$: 3600~2600, 1715, 1280, 1140

NMR (CDCl$_3$) δ: 3.89 (3H, s), 3.98 (3H, s), 4.63 (2H, d, 6 Hz), 5.29 (1H, dd, 10 Hz, 2 Hz, cis), 5.42 (1H, q, 16 Hz, 2 Hz, trans), 5.97~6.18 (1H, m), 6.86 (1H, d, 8 Hz), 6.96 (1H, d, 16 Hz), 7.07 (1H, s), 7.27 (1H, t, 8 Hz), 7.56 (1H, d, 16 Hz), 7.85 (1H, q, 8 Hz, 2 Hz).

EXAMPLE 57

Methyl (E)-2-(4-cyanostyryl)benzimidazole-4-carboxylate

Yellowish brown crystals, m.p. 197°–198° C. (EtOH).

Elem. Anal. (C$_{18}$H$_{13}$N$_3$O$_2$). Calcd (%): C: 71.28 H: 4.32 N: 13.85. Found (%): C: 71.24 H: 4.01 N: 13.90.

IR (KBr) cm$^{-1}$: 3500~2600, 2240, 1730, 1290, 1135.

NMR (CDCl$_3$) δ: 4.03 (3H, s), 7.24 (1H, d, 16 Hz), 7.33 (1H, t, 8 Hz), 7.58~7.75 (5H, m), 7.92 (1H, dd, 8 Hz, 1.5 Hz), 7.97 (1H, dd, 8 Hz, 1.5 Hz), 8.00~10.70 (1H, m).

EXAMPLE 58

Methyl (E)-2-styrylbenzimidazole-4-carboxylate

Yellow crystals, m.p. 84°–90° C. (Et$_2$O).

Elem. Anal. (C$_{17}$H$_{14}$N$_2$O$_2$). Calcd (%): C: 73.15 H: 5.29 N: 9.80. Found (%): C: 73.00 H: 5.33 N: 9.64.

IR (KBr) cm$^{-1}$: 3500~2300, 1730, 1280, 1135.

NMR (CDCl$_3$) δ: 4.01 (3H, s), 7.14 (1H, d, 16 Hz), 7.29 (1H, t, 8 Hz), 7.34~7.60 (5H, m), 7.66 (1H, d, 16 Hz), 7.87 (1H, dd, 8 Hz, 1.5 Hz), 7.94 (1H, dd, 8 Hz, 1.5 Hz), 9.73~10.80 (1H, m).

EXAMPLE 59

Methyl (E)-2-(3-fluoro-4-methoxystyryl)benzimidazole-4-carboxylate

Pale yellow crystals, m.p. 97°–99° C. (Et$_2$O).

Elem. Anal. (C$_{18}$H$_{15}$FN$_2$O$_3$). Calcd (%): C: 66.25 H: 4.63 N: 8.58. Found (%): C: 66.00 H: 4.51 N: 8.54.

IR (KBr) cm$^{-1}$: 3500~2600, 1730, 1280, 1130.

NMR (CDCl$_3$) δ: 3.91 (3H, s), 4.01 (3H, s), 6.93 (1H, t, 8 Hz), 6.96 (1H, d, 16 Hz), 7.28 (1H, t, 8 Hz), 7.19~7.36 (2H, m), 7.56 (1H, d, 16 Hz), 7.86 (1H, dd, 8 Hz, 1.5 Hz), 7.92 (1H, dd, 8 Hz, 1.5 Hz), 9.58~10.52 (1H, m).

EXAMPLE 60

Methyl (E)-2-(2,5-dimethoxystyryl)benzimidazole-4-carboxylate

Pale yellow crystals, m.p. 90°–92° C. (EtOH).

Elem. Anal. (C$_{19}$H$_{18}$N$_2$O$_4$.0.5H$_2$O.0.2EtOH). Calcd (%): C: 65.35 H: 5.71 N: 7.86. Found (%): C: 65.40 H: 5.71 N: 7.64.

IR (KBr) cm$^{-1}$: 3600~2600, 1730, 1280, 1135.

NMR (CDCl$_3$) δ: 3.79 (3H, s), 3.85 (3H, s), 4.00 (3H, s), 6.84 (2H, s), 7.11 (1H, s), 7.27 (1H, d, 16 Hz), 7.28 (1H, t, 8 Hz), 7.87 (1H, d, 16 Hz), 7.86 (1H, dd, 8 Hz, 2 Hz), 7.94 (1H, dd, 8 Hz, 2 Hz).

EXAMPLE 61

Methyl (E)-2-[3-methoxy-4-(2-propynyloxy)styryl]-benzimidazole-4-carboxylate

Pale yellow crystals, mp. 180°–182° C. (EtOH).

Elem. Anal. (C$_{21}$H$_{18}$N$_2$O$_4$). Calcd (%): C: 69.60 H: 5.01 N: 7.73. Found (%): C: 69.54 H: 4.87 N: 7.65.

IR (KBr) cm$^{-1}$: 3500~2600, 1710, 1290, 1140.

NMR (CDCl$_3$) δ: 2.54 (1H, t, 1.5 Hz), 3.93 (3H, s), 4.02 (3H, s), 4.81 (2H, d, 1.5 Hz), 7.04 (1H, d, 8 Hz), 7.05 (1H, d, 16 Hz), 7.12 (1H, s), 7.09~7.18 (1H, m), 7.29 (1H, t, 8 Hz), 7.60 (1H, d, 16 Hz), 7.87 (1H, dd, 8 Hz, 1.5 Hz), 7.94 (1H, dd, 8 Hz, 1.5 Hz), 10.36~10.54 (1H, m).

EXAMPLE 62

Methyl (E)-2-(4-allyloxy-3-ethoxystyryl)benzimidazole-4-carboxylate

Pale yellow crystals, m.p. 106°–108° C. (AcOEt-Et$_2$O).

Elem. Anal. (C$_{22}$H$_{22}$N$_2$O$_4$). Calcd (%): C: 69.82 H: 5.86 N: 7.40. Found (%): C: 69.83 H: 5.80 N: 7.32.

IR (KBr) cm$^{-1}$: 3500~2600, 1730, 1270, 1140.

NMR (CDCl$_3$) δ: 1.47 (3H, t, 8 Hz), 4.00 (3H, s), 4.11 (2H, q, 8 Hz), 4.64 (2H, d, 6 Hz), 5.29 (1H, dd, 10 Hz, 1.5 Hz), 5.41 (1H, dd, 16 Hz, 1.5 Hz), 6.98~6.18 (1H, m), 6.87 (1H, d, 8 Hz), 7.00 (1H, d, 16 Hz), 7.08 (1H, s), 7.02-7.15 (1H, m), 7.28 (1H, t, 8 Hz), 7.59 (1H, d, 16 Hz), 7.87 (1H, dd, 8 Hz, 1.5 Hz), 7.83 (1H, dd, 8 Hz, 1.5 Hz), 9.54~10.84 (1H, m).

EXAMPLE 63

Methyl (E)-2-(3,4-dimethoxystyryl)benzimidazole-4-carboxylate methanesulfonate

Yellow powder, m.p. 212°–216° C. (EtOH).

Elem. Anal. (C$_{19}$H$_{18}$N$_2$O$_4$.CH$_4$O$_3$S.0.7H$_2$O). Calcd (%): C: 53.73 H: 5.28 N: 6.27 S: 7.17. Found (%): C: 53.79 H: 5.50 N: 6.25 S: 7.99.

IR (KBr) cm$^{-1}$: 3600~2400, 1730, 1265, 1160, 1140, 1020, 750.

NMR (DMSO-d$_6$) δ: 2.47 (3H, s), 3.84 (3H, s), 3.87 (3H, s), 4.03 (3H, s), 7.05 (1H, d, 8 Hz), 7.20-7.34 (2H, m), 7.43 (1H, d, 16 Hz), 7.62 (1H, t, 8 Hz), 7.98~8.11 (3H, m).

EXAMPLE 64

Methyl (E)-2-(3,4-dimethoxystyryl)benzimidazole-4-carboxylate ethanesulfonate

Yellow crystals, mp. 168°–172° C. (MeOH).

Elem. Anal. (C$_{19}$H$_{18}$N$_2$O$_4$.C$_2$H$_6$O$_3$S.H$_2$O). Calcd (%): C: 54.07 H: 5.62 N: 6.00 S: 6.87. Found (%): C: 53.98 H: 5.77 N: 5.98 S: 7.01.

IR (KBr) cm$^{-1}$: 3600~2400, 1730, 1265, 1165, 1140, 1035, 755.

NMR (DMSO-d$_6$) δ: 1.15 (3H, t, 7 Hz), 2.57 (2H, q, 7 Hz), 3.83 (3H, s), 3.86 (3H, s), 4.02 (3H, s), 7.03 (1H, d, 8 Hz), 7.17~7.36 (2H, m), 7.45 (1H, d, 16 Hz), 7.60 (1H, t, 8 Hz), 7.97~8.11 (3H, m), 13~8 (broad.)

EXAMPLE 65

Methyl (E)-2-(3,4-dimethoxystyryl)benzimidazole-4-carboxylate d-10-camphorsulfonate Yellow crystals, m.p. 228°–230° C. (MeOH).

Elem. Anal. ($C_{19}H_{18}N_2O_4 \cdot C_{10}H_{16}O_4S \cdot 0.7H_2O$). Calcd (%): C: 59.72 H: 6.12 N: 4.80 S: 5.50. Found (%): C: 59.87 H: 6.25 N: 4.86 S: 5.78.

IR (KBr) cm$^{-1}$: 3600~2400, 1730, 1265, 1160, 1140, 1040, 755.

NMR (DMSO-d$_6$) δ: 0.76 (3H, s), 1.06 (3H, s), 1.20~1.44 (2H, m), 1.80 (1H, d, 18 Hz), 1.73~1.98 (2H, m), 2.24 (1H, dt, 8 Hz, 4 Hz), 2.51 (1H, d, 15 Hz), 2.60~2.81 (1H, m), 2.99 (1H, d, 15 Hz), 3.84 (3H, s), 3.87 (3H, s), 4.03 (3H, s), 7.06 (1H, d, 8 Hz), 7.21~7.36 (1H, m), 7.42 (1H, d, 16 Hz), 7.61 (1H, t, 8 Hz), 7.98~8.11 (1H, m), 13~8 (2H, broad.).

EXAMPLE 66

Methyl (E)-2-(3,4-dimethoxystyryl)benzimidazole-4-carboxylate 1-naphthalenesulfonate Yellow crystals, mp. 215°–218° C. (MeOH).

Elem. Anal. ($C_{19}H_{18}N_2O_4 \cdot C_{10}H_8O_3S \cdot 0.5H_2O$). Calcd (%): C: 62.69 H: 4.90 N: 5.04 S: 5.77. Found (%): C: 62.70 H: 4.96 N: 5.04 S: 6.23.

IR (KBr) cm$^{-1}$: 3600~2500, 1735, 1265, 1165, 1140, 1045, 800, 760.

NMR (DMSO-d$_6$) δ: 3.84 (3H, s), 3.85 (3H, s), 4.01 (3H, s), 7.06 (1H, d, 8 Hz), 7.17~7.52 (6H, m), 7.61 (1H, t, 8 Hz), 7.81~8.08 (6H, m), 8.80~8.90 (1H, m), 15~8 (broad.).

EXAMPLE 67

Methyl (E)-2-(3,4-dimethoxystyryl)benzimidazole-4-carboxylate sulfate

Yellow powder, m.p. 263°–266° C.(decompn.)(EtOH).

Elem. Anal. ($C_{19}H_{18}N_2O_4 \cdot H_2SO_4 \cdot 0.5H_2O$). Calcd (%): C: 51.23 H: 4.75 N: 6.29 S: 7.20. Found (%): C: 51.22 H: 4.78 N: 6.30 S: 7.52.

IR (KBr) cm$^{-1}$: 3500~2400, 1725, 1265, 1140, 755.

NMR (DMSO-d$_6$) δ: 3.84 (3H, s), 3.87 (3H, s), 4.04 (3H, s), 7.06 (1H, d, 8 Hz), 7.20~7.33 (2H, m), 7.42 (1H, d, 16 Hz), 7.63 (1H, t, 8 Hz), 7.97~8.11 (3H, m), 6~12 (broad.).

EXAMPLE 68

Methyl (E)-2-(3,4-dimethoxystyryl)benzimidazole-4-carboxylate nitrate

Yellow powder, m.p. 198°–201° C.(decompn.)(EtOH).

Elem. Anal. ($C_{19}H_{18}N_2O_4 \cdot HNO_3 \cdot 0.2H_2O$). Calcd (%): C: 56.35 H: 4.83 N: 10.38. Found (%): C: 56.29 H: 4.75 N: 10.48.

IR (KBr) cm$^{-1}$: 3600~2500, 1725, 1265, 1140, 750.

NMR (DMSO-d$_6$) δ: 3.85 (3H, s), 3.88 (3H, s), 4.02 (3H, s), 2.8~5.6 (broad. disappeared by D$_2$O) 7.10 (1H, d, 8 Hz), 7.23~7.33 (2H, m), 7.33 (1H, d, 16 Hz), 7.60 (1H, t, 8 Hz), 7.94~8.08 (3H, m).

EXAMPLE 69

Methyl (E)-2-(3,4-dimethoxystyryl)benzimidazole-4-carboxylate hydrobromide

Yellow powder, m.p. 214°–218° C. (EtOH).

Elem. Anal. ($C_{19}H_{18}N_2O_4 \cdot HBr \cdot 0.8H_2O$). Calcd ( C: 52.62 H: 4.79 N: 6.46. Found (%): C: 52.59 H: 4.8 6.47.

IR (KBr) cm$^{-1}$: 3500~2500, 1725, 1265, 1140,

NMR (DMSO-d$_6$) δ: 3.85 (3H, s), 3.88 (3H, s), (3H, s), 2.8~4.6 (broad. disappeared by D$_2$O) 7.10 d, 8 Hz), 7.22~7.36 (2H, m), 7.35 (1H, d, 16 Hz), (1H, t, 8 Hz), 7.96~8.08 (3H, m).

EXAMPLE 70

Methyl (E)-2-(3,4-dimethoxystyryl)benzimidazole-4-carbo late hydrochloride

Yellow powder, m.p. 190°–193° C. (decon (EtOH).

Elem. Anal. ($C_{19}H_{18}N_2O_4 \cdot HCl \cdot 1.2H_2O$). Calcd C: 57.56 H: 5.44 N: 7.07 Cl: 8.94. Found (%): C: H: 5.41 N: 7.12 Cl: 9.03.

IR (KBr) cm$^{-1}$: 3500~2300, 1725, 1265, 1140,

NMR (DMSO-d$_6$) δ: 3.85 (3H, s), 3.88 (3H, s), (3H, s), 4.8~2.8 (broad. disappeared by D$_2$O) 7.09 d, 8 Hz), 7.19~7.27 (2H, m), 7.41 (1H, d, 16 Hz), (1H, t, 8 Hz), 7.97~8.07 (2H, m), 8.21 (1H, d, 16

EXAMPLE 71

Methyl (E)-2-(3-ethoxy-4-methoxystyryl)benzimidazole-4 boxylate

Pale yellow crystals, m.p. 154°–156° C. (EtOH

Elem. Anal. ($C_{20}H_{20}N_2O_4$). Calcd (%): C: 68. 5.72 N: 7.95. Found (%): C: 68.01 H: 5.68 N: 7.9ϵ

IR (KBr) cm$^{-1}$: 3500~2600, 1700, 1270, 1140.

NMR (CDCl$_3$) δ: 1.49 (3H, t, 8 Hz), 3.90 (3H, s) (3H, s), 4.14 (2H, q, 8 Hz), 6.86 (1H, d, 8 Hz), 7.0C d, 16 Hz), 7.28 (1H, t, 8 Hz), 7.59 (1H, d, 16 Hz) (1H, d, 8 Hz), 7.92 (1H, d, 8 Hz), 8.44~11.24 (1H

EXAMPLE 72

Methyl (E)-2-[4-(2-methoxyethoxy)-3-methoxystyryl]-b zimidazole-4-carboxylate

Yellow crystals, m.p. 167°–169° C. (AcOEt-Et

Elem. Anal. ($C_{21}H_{22}N_2O_5$). Calcd (%): C: 65. 5.80 N: 7.33. Found (%): C: 65.87 H: 5.85 N: 7.2:

IR (KBr) cm$^{-1}$: 3600~2600, 1725, 1270, 1140.

NMR (CDCl$_3$) δ: 3.44 (3H, s), 3.78 (2H, t, 6 Hz) (3H, s), 3.99 (3H, s), 4.19 (2H, t, 6 Hz), 6.88 (1H Hz), 7.02 (1H, d, 16 Hz), 7.00~7.12 (2H, m), 7.28 t, 8 Hz), 7.60 (1H, d, 16 Hz), 7.85 (1H, dd, 8 Hz, 1.⁵ 7.92 (1H, dd, 8 Hz, 1.5 Hz), 9.68~11.36 (1H, m).

EXAMPLE 73

Methyl (E)-2-(2-allyloxy-3-methoxystyryl)benzimidazole-4 boxylate

Pale yellow crystals, m.p. 148°–150° C. (AcOE

Elem. Anal. ($C_{21}H_{20}N_2O_4$). Calcd (%): C: 69.2 5.53 N: 7.69. Found (%): C: 69.45 H: 5.53 N: 7.67

IR (KBr) cm$^{-1}$: 3500~2600, 1730, 1280, 1140.

NMR (CDCl₃) δ: 3.88 (3H, s), 4.02 (3H, s), 4.59 (2H, d, 8 Hz), 5.27 (1H, d, 10 Hz, cis-configuration), 5.40 (1H, d, 16 Hz, trans-configuration), 6.04~6.24 (1H, m), 6.90 (1H, dd, 8 Hz, 1.5 Hz), 7.08 (1H, t, 8 Hz), 7.23 (1H, d, 8 Hz), 7.26 (1H, d, 16 Hz), 7.27 (1H, t, 8 Hz), 7.87 (1H, dd, 8 Hz, 1.5 Hz), 7.90 (1H, d, 16 Hz), 7.94 (1H, dd, 8 Hz, 1.5 Hz), 9.80~10.70 (1H, m).

EXAMPLE 74

Methyl (E)-2-(3,4-dichlorostyryl)benzimidazole-4-carboxylate

Pale yellow crystals, m.p. 171°-172° C. (AcOEt).
Elem. Anal. (C₁₇H₁₂Cl₂N₂O₂). Calcd (%): C: 58.81 H: 3.48 N: 8.07. Found (%): C: 58.99 H: 3.33 N: 8.04.
IR (KBr) cm⁻¹: 3500~2600, 1680, 1285, 1140.
NMR (CDCl₃) δ: 4.01 (3H, s), 7.07 (1H, d, 16 Hz), 7.30 (1H, t, 8 Hz), 7.30 (1H, d, 8Hz), 7.41 (1H, d, 8 Hz), 7.53 (1H, d, 16 Hz), 7.55 (1H, d, 1.5 Hz), 7.89 (1H, dd, 8 Hz, 1.5 Hz), 7.95 (1H, dd, 8 Hz, 1.5 Hz), 10.28~10.82 (1H, m).

EXAMPLE 75

Methyl (E)-2-(2,3-dichlorostyryl)benzimidazole-4-carboxylate

Pale yellow crystals, m.p. 158°-160° C. (AcOEt).
Elem. Anal. (C₁₇H₁₂Cl₂N₂O₂). Calcd (%): C: 58.81 H: 3.48 N: 8.07. Found (%): C:59.06 H: 3.41 N: 8.12.
IR (KBr) cm⁻¹: 3600~2600, 1715, 1275, 1150.
NMR (CDCl₃) δ: 4.02 (3H, s), 7.14 (1H, d, 16 Hz), 7.23 (1H, d, 8 Hz), 7.30 (1H, t, 8 Hz), 7.42 (1H, dd, 8 Hz, 1.5 Hz), 7.56 (1H, dd, 8 Hz, 1.5 Hz), 7.89 (1H, dd, 8 Hz, 1.5 Hz), 7.96 (1H, dd, 8 Hz, 1.5 Hz), 7.96 (1H, d, 16 Hz), 9.91~10.84 (1H, m).

EXAMPLE 76

Methyl (E)-2-(2,5-dimethylstyryl)benzimidazole-4-carboxylate

Pale yellow crystals, m.p. 167°-168° C. (AcOEt-Et₂O).
Elem. Anal. (C₁₉H₁₈N₂O₂). Calcd (%): C: 74.49 H: 5.92 N: 9.15. Found (%): C: 74.55 H: 5.85 N: 9.13.
IR (KBr) cm⁻¹: 3600~2500, 1740, 1280, 1140.
NMR (CDCl₃) δ: 2.34 (3H, s), 2.43 (3H, s), 4.00 (3H, s), 7.05 (1H, d, 16 Hz), 7.07 (2H, s), 7.30 (1H, t, 8 Hz), 7.41 (1H, s), 7.88 (1H, d, 8 Hz), 7.91 (1H, d, 16 Hz), 7.96 (1H, d, 8 Hz), 9.86~10.80 (1H, m).

EXAMPLE 77

Methyl (E)-2-(4-methylstyryl)benzimidazole-4-carboxylate

Pale yellow crystals, m.p. 165°-167° C. (AcOEt-Et₂O).
Elem. Anal. (C₁₈H₁₆N₂O₂). Calcd (%): C: 73.95 H: 5.52 N: 9.58. Found (%): C: 74.22 H: 5.49 N: 9.67.
IR (KBr) cm⁻¹: 3600~2600, 1725, 1280, 1130.
NMR (CDCl₃) δ: 2.36 (3H, s), 4.00 (3H, s), 7.08 (1H, d, 16 Hz), 7.18 (2H, d, 8 Hz), 7.28 (1H, t, 8 Hz), 7.48 (2H, d, 8 Hz), 7.62 (1H, d, 16 Hz), 7.88 (1H, dd, 8 Hz, 1.5 Hz), 7.92 (1H, dd, 8 Hz, 1.5 Hz), 9.37~10.32 (1H, m).

EXAMPLE 78

Methyl (E)-2-(4-chlorostyryl)benzimidazole-4-carboxylate

Yellow crystals, m.p. 172°-173° C. (AcOEt-Et₂O).
Elem. Anal. (C₁₇H₁₃ClN₂O₂). Calcd (%): C: 65.29 H: 4.19 N: 8.96. Found (%): C: 65.60 H: 4.02 N: 8.94.
IR (KBr) cm⁻¹: 3500~2600, 1715, 1275, 1145.
NMR (CDCl₃) δ: 3.99 (3H, s), 7.07 (1H, d, 16 Hz), 7.30 (1H, t, 8 Hz), 7.33 (2H, d, 8 Hz), 7.42 (2H, d, 8 Hz), 7.59 (1H, d, 16 Hz), 7.87 (1H, dd, 8 Hz, 1.5 Hz), 7.93 (1H, dd, 8 Hz, 1.5 Hz), 9.63~10.27 (1H, m).

EXAMPLE 79

Methyl (E)-2-(2,4-dimethoxystyryl)benzimidazole-4-carboxylate

Yellow crystals, m.p. 164°-165° C. (AcOEt).
Elem. Anal. (C₁₉H₁₈N₂O₄). Calcd (%): C: 67.45 H: 5.36 N: 8.45. Found (%): C: 67.78 H: 5.26 N: 8.34.
IR (KBr) cm⁻¹: 3500~2600, 1705, 1280.
NMR (CDCl₃) δ: 3.84 (3H, s), 3.87 (3H, s), 4.01 (3H, s), 6.46 (1H, d, 1.5 Hz), 6.52 (1H, dd, 8 Hz, 1.5 Hz), 7.18 (1H, d, 16 Hz), 7.26 (1H, t, 8 Hz), 7.82 (1H, d, 16 Hz), 7.84 (1H, dd, 8 Hz, 1.5 Hz), 7.92 (1H, dd, 8 Hz, 1.5 Hz), 9.97~10.90 (1H, m).

EXAMPLE 80

Methyl (E)-2-(2,3-dimethoxystyryl)benzimidazole-4-carboxylate

Yellow crystals, m.p. 197°-199° C. (AcOEt).
Elem. Anal. (C₁₉H₁₈N₂O₄). Calcd (%): C: 67.45 H: 5.36 N: 8.45. Found (%): C: 67.55 H: 5.27 N: 8.35.
IR (KBr) cm⁻¹: 3500~2600, 1730, 1275, 1139.
NMR (CDCl₃) δ: 3.88 (3H, s), 3.91 (3H, s), 4.01 (3H, s), 6.90 (1H, dd, 8 Hz, 1.5 Hz), 7.07 (1H, t, 8 Hz), 7.22 (1H, dd, 8Hz, 1.5 Hz), 7.25 (1H, d, 16 Hz), 7.30 (1H, t, 8 Hz), 7.88 (1H, dd, 8 Hz, 1.5 Hz), 7.90 (1H, d, 16 Hz), 7.95 (1H, dd, 8 Hz, 1.5 Hz), 9.71~11.28 (1H, m).

EXAMPLE 81

Methyl (E)-2-(3,4-dimethoxystyryl)-1-methylbenzimidazole-4-carboxylate

Sodium hydride (1.06 g) was suspended in 30 ml of dry tetrahydrofuran and, with ice cooling, a solution of 6.77 g methyl (E)-2-(3,4-dimethoxystyryl)benzimidazole-4-carboxylate obtained in Example 1 in 23 ml of dry tetrahydrofuran was dropped thereinto with stirring gradually. The mixture was stirred for 3 hours at room temperature, a solution of 3.48 g of methyl iodide in 5 ml of tetrahydrofuran (dried) was added thereto, and the mixture was stirred for 15 hours at room temperature. Small amount of methanol is added to decompose sodium hydride, the solvent was evaporated in vacuo, and the residue was extracted with water-chloroform. The chloroform-layer was washed with water, then dried with anhydrous magnesium sulfate, and chloroform was evaporated in vacuo. Methanol was added to the rubbery residue to give crystals. Those were collected by filtration to give 4.64 g of yellow crystals, m.p. 187°-189° C. (methanol).

Elem. Anal. (C₂₀H₂₀N₂O₄). Calcd (%): C: 68.17 H: 5.72 N: 7.95. Found (%): C: 68.43 H: 5.74 N: 7.97.
IR (IBr) cm⁻¹: 1690, 1265, 1140, 755.
NMR (CDCl₃) δ: 3.89 (3H, s), 3.93 (3H, s), 3.96 (3H, s), 4.07 (3H, s), 6.89 (1H, d, J=8 Hz), 6.97 (1H, d, J=16 Hz) 7.15 (1H, d, J=1.5 Hz), 7.22 (1H, dd, J=8 Hz, 1,5 Hz), 7.28 (1H, t, J=8 Hz), 7.49 (1H, dd, J=8 Hz, 1.5 Hz), 7.97 (1H, dd, J=8 Hz, 1,5 Hz), 8.06 (1H, d, J=16 Hz).

By the similar manner as Example 81, the compounds of Examples 82 and 83 were obtained.

EXAMPLE 82

Methyl (E)-2-(3,4-dimethoxystyryl)-1-acetylbenzimidazole-4-carboxylate

M.p. 161°–163° C. (chloroform-ethyl acetate).
Elem. Anal. ($C_{21}H_{20}N_2O_5$). Calcd (%): C: 66.31 H: 5.30 N: 7.36. Found (%): C: 66.71 H: 5.14 N: 7.47.
IR (KBr) cm$^{-1}$: 1715, 1695, 1260, 1140, 750.
NMR (CDCl$_3$) δ: 2.87 (3H, s), 3.93 (3H, s), 3.95 (3H, s), 4.06 (3H, s), 6.89 (1H, d, J=8 Hz), 7.14 (1H, d, J=1.5 Hz), 7.23 (1H, dd, J=8 Hz, 1.5 Hz), 7.37 (1H, t, J=8 Hz), 7.49 (1H, d, J=16 Hz), 8.00 (2H, dd, J=8 Hz, 1.5 Hz), 8.06 (1H, d, J=16 Hz).

EXAMPLE 83

Methyl (E)-2-(3,4-dimethoxystyryl)-1-methanesulfonylbenzimidazole-4-carboxylate

M.p. 182°–184° C. (decompn) (chloroform-ethyl acetate).
Elem. Anal. ($C_{20}H_{20}N_6O_6S$). Calcd (%): C: 57.68 H: 4.84 N: 6.73. Found (%): C: 57.55 H: 4.84 N: 6.80.
IR (KBr) cm$^{-1}$: 1710, 1375, 1365, 1265, 1140, 750.
NMR (CDCl$_3$) δ: 3.22 (3H, s), 3.94 (3H, s), 3.96 (3H, s), 4.06 (3H, s), 6.90 (1H, d, J=8 Hz), 7.16 (1H, d, J=1.5 Hz), 7.26 (1H, dd, J=8 Hz, 1.5 Hz), 7.39 (1H, t, J=8 Hz), 7.60 (1H, d, J=16 Hz), 8.03 (1H, dd, J=8 Hz, 1.5 Hz), 8.15 (1H, dd, J=8 Hz, 1.5 Hz), 8.16 (1H, d, J=16 Hz).

EXAMPLE 84

Methyl (Z)-2-(3,4-dimethoxystyryl)benzimidazole-4-carboxylate

Methyl (E)-2-(3,4-dimethoxystyryl)benzimidazole-4-carboxylate (5.0 g) obtained in Example 1 was dissolved in 400 ml of methanol, the solution was irradiated with a light for 2 days from a 300 watts tungusten lamp, then the reaction solution was concentrated in vacuo, the oily residue was subjected to a silica gel column chromatography, the column was eluted with n-hexane-ethyl acetate (8:2), the eluate was concentrated in vacuo, the resulting yellow oil was dissolved in ether, and the solution was allowed to stand at 5° C. to give 1.39 g of pale yellow crystals, m.p. 87°–89° C. (ether).
Elem. Anal. ($C_{19}H_{18}N_2O_4$). Calcd (%): C: 67.45 H: 5.36 N: 8.28. Found (%): C: 67.64 H: 5.44 N: 8.24.
IR (KBr) cm$^{-1}$: 3300~2500, 1725, 1270, 1130, 750.
NMR (CDCl$_3$) δ: 3.82 (3H, s), 3.85 (3H, s), 3.95 (3H, s), 6.69 (1H, d, J=12.4 Hz), 6.97 (1H, d, J=8 Hz), 7.05 (1H, d, J=12.4 Hz), 7.07 (1H, dd, J=8 Hz, 1.5 Hz), 7.28 (1H, d, J=1.5 Hz), 7.28 (1H, t, J=8 Hz), 7.88 (1H, dd, J=8 Hz 1.5 Hz), 7.92 (1H, dd, J=8 Hz), 9.94~10.10 (1H, br).

EXAMPLE 85

Methyl 2-(3,4-dimethoxyphenethyl)benzimidazole-4-carboxylate

Methyl (E)-2-(3,4-dimethoxystyryl)benzimidazole-4-carboxylate (5.0 g) obtained in Example 1 was dissolved in a mixed solvent of tetrahydrofuran and methanol (1:1), 500 mg of 5% palladium-carbon was added, and then subjected to a catalytic reduction at room temperature and ordinary pressure. The reaction was completed after absorbing about one equivalent of hydrogen. The reaction solution was filtered, the filtrate was concentrated in vacuo, the residue was subjected to a silica gel columnchromatography, the column was eluted with a 7:3 mixture of n-hexane and ethyl acetate, colorless oil obtained as an eluate was crystallized with a mixed solvent of n-hexane and ethyl acetate, and recrystallized from n-hexane-ethyl acetate to give 4.43 g of colorless crystals, m.p. 101°–103° C.
Elem. Anal. ($C_{19}H_{20}N_2O_4$). Calcd (%): C: 67.05 H: 5.92 N: 8.23. Found (%): C: 67.31 H: 5.99 N: 8.25.
IR (KBr) cm$^{-1}$: 3500~2500, 1710, 1280, 1140, 750.
NMR (CDCl$_3$) δ: 3.08~3.34 (4H, m), 3.79 (3H, s), 3.86 (3H, s), 3.96 (3H, s), 6.70~6.86 (3H, m), 7.26 (1H, t, J=8 Hz), 7.84 (1H, dd, J=8 Hz, 1.5 Hz), 7.90 (1H, dd, J=8 Hz, 1.5 Hz), 9.86~10.07 (1H, br).

By the same manner as Example 1, the following substances were obtained.

EXAMPLE 86

Methyl (E)-2-(3,4-dimethoxystyryl)benzimidazole-4-carboxylate benzenesulfonate

Yellow crystals, m.p. 170°–173° C.
Elem. Anal. ($C_{19}H_{18}N_2O_4 \cdot C_6H_5SO_3H$).
Calcd (%): C: 60.47 H: 4.87 N: 5.64 S: 6.46. Found (%): C: 58.34 H: 5.03 N: 5.46 S: 6.50.
IR (KBr) cm$^{-1}$: 3420, 3200~2500, 1725, 1300, 1030, 755.
NMR (DMOS-d$_6$) δ: 3.84 (3H, s), 3.86 (3H, s), 4.01 (3H, s), 7.08 (1H, d, 8 Hz), 7.20~7.46 (6H, m), 7.56~7.70 (3H, m), 7.96~8.10 (3H, m), 14.0~8.0 (2H, br.).

EXAMPLE 87

Methyl (E)-2-(4-allyloxy-3-methoxystyryl)benzimidazole-4-carboxylate phosphate

M.p. 278°–280° C. (decompn.), yellow powder.
Elem. Anal. ($C_{21}H_{23}N_2O_8P$)
Calcd (%): C: 54.55 H: 5.01 N: 6.06 Found (%): C: 53.95 H: 4.95 N: 6.04
IR (KBr) cm$^{-1}$: 3600~2200, 1720, 1270, 1090, 755.
NMR (DMSO-d$_6$) δ: 3.86 (3H, s), 3.97 (3H, s), 4.60 (2H, dt, 5 Hz, 1 Hz), 5.22~5.48 (2H, m), 5.95~6.16 (1H, m), 7.02 (1H, d, 8 Hz), 7.12~7.36 (4H, m), 7.72~7.90 (3H, m), 12.20~12.40 (1H, broad s).

EXAMPLE 88

Methyl (E)-2-(4-dimethylaminostyryl)benzimidazole-4-carboxylate

M.p. 232°–234° C., yellow crystals.
Elem. Anal. ($C_{19}H_{19}N_3O_2$).
Calcd (%): C: 71.01 H: 5.96 N: 13.07. Found (%): C: 71.01 H: 5.96 N: 13.05.
IR (KBr) cm$^{-1}$: 3400, 1720, 1275, 1139.
NMR (CDCl$_3$) δ: 3.02 (6H, s), 4.01 (3H, s), 6.70 (2H, d, 8 Hz), 6.92 (1H, d, 16 Hz), 7.26 (1H, t, 8 Hz), 7.47 (2H, d, 8 Hz), 7.58 (1H, d, 16 Hz), 7.83 (2H, dd, 8 Hz, 1.5 Hz), 7.90 (1H, dd, 8 Hz, 1.5 Hz), 10.30~10.40 (1H, bs).

EXAMPLE 89

Methyl (E)-2-(4-difluoromethoxystyryl)benzimidazole-4-carboxylate

M.p. 106°–108° C., colorless crystals.
Elem. Anal. ($C_{18}H_{14}F_2N_2O_3$).
Calcd (%): C: 62.79 H: 4.10 N: 8.14. Found (%): C: 62.88 H: 4.01 N: 8.17.
IR (KBr) cm$^{-1}$: 3450, 1700, 1275, 1120.
NMR (CDCl$_3$) δ: 4.02 (3H, s), 6.55 (1H, t, 74 Hz), 7.08 (1H, d, 16 Hz), 7.14 (2H, d, 8 Hz), 7.31 (1H, t, 8 Hz), 7.55 (2H, d, 8 Hz), 7.64 (1H, d, 16 Hz), 7.89 (1H, dd, 8 Hz, 1.5 Hz), 7.95 (1H, dd, 8 Hz, 1.5 Hz), 9.53~10.43 (3H, bs).

EXAMPLE 90

Methyl (E)-2-(4-difluoromethoxystyryl)benzimidazole-4-carboxylate phosphate

M.p. 272°–274° C., pale yellow crystals
Elem. Anal. ($C_{18}H_{14}F_2N_2O_3H_3PO_4$).
Calcd (%): C: 48.88 H: 3.87 N: 6.33. Found (%): C: 48.82 H: 3.83 N: 6.39.
IR (KBr) cm$^{-1}$: 3400, 2500~1770, 1725 1300.
NMR (DMSO-d$_6$) δ: 3.98 (3H, s), 7.30 (1H, t, 74 Hz), 7.21~7.36 (3H, m), 7.37 (1H, d, 16 Hz), 7.73 (2H, d, 8 Hz), 7.77~7.93 (3H, m), 12.31~12.57 (1H, bs).

EXAMPLE 91

Methyl (E)-2-[4-(2-piperidinoethoxy)styryl]benzimidazole-4-carboxylate

M.p. 52°–55° C., pale yellow powder.
Elem. Anal. ($C_{24}H_{27}N_3O_3 \cdot 1/5H_2O$).
Calcd (%): C: 70.46 H: 6.75 N: 10.27. Found (%): C: 70.48 H: 6.86 N: 10.27.
IR (KBr) cm$^{-1}$: 1700, 1510, 1250, 1030.
NMR (CDCl$_3$) δ: 1.37~1.70 (6H, m), 2.45~2.60 (4H, m), 2.79 (2H, t, 6 Hz), 4.01 (3H, s), 4.14 (2H, t, 6 Hz), 6.92 (2H, d, 8 Hz), 6.99 (1H, d, 16 Hz), 7.27 (1H, t, 8 Hz), 7.49 (2H, d, 8 Hz), 7.60 (1H, d, 16 Hz), 7.85 (1H, dd, 8 Hz, 1.5 Hz), 7.92 (1H, dd, 8 Hz, 1.5 Hz), 10.34~10.47 (1H, bs).

What is claimed is:

1. A compound of the formula (I):

or a pharmaceutically acceptable acid addition salt thereof wherein $R^1$ is hydrogen or lower alkyl; $R^2$ is $$-\underset{\underset{R^6}{|}}{\overset{\overset{R^4}{|}}{C}}-\underset{\underset{R^7}{|}}{\overset{\overset{R^5}{|}}{C}}-Ar, \quad -\underset{\underset{R^6}{|}}{C}=\underset{\underset{R^7}{|}}{C}-Ar$$

or —C≡C—Ar wherein Ar is phenyl unsubstituted or substituted by one to three substituents selected from the group consisting of:

(a) halo;
(b) lower alkyl;
(c) hydroxy;
(d) lower alkoxy unsubstituted or substituted by lower alkoxy, acetyloxy, amino or mono- or di-lower alkylamino;
(e) aralkyloxy wherein the alkyl moiety is a lower alkyl moiety;
(f) lower alkenyloxy;
(g) lower alkynyloxy;
(h) difluoromethoxy;
(i) lower alkylamino;
(j) methylenedioxy;
(k) trifluoromethyl;
(l) cyano;
(m) lower alkylthio; and
(n) lower alkylsulfinyl;

$R^4$, $R^5$, $R^6$, and $R^7$ are hydrogen or lower alkyl or $R^4$ and $R^5$ together with the carbon atoms to which they are attached form a cyclopropyl ring; and $R^3$ is hydrogen, lower alkyl, acyl or alkylsulphonyl.

2. A compound according to claim 1 wherein $R^1$ is hydrogen, methyl, ethyl, n-propyl, isopropyl, n-butyl, isobutyl, sec-butyl or tert-butyl.

3. A compound according to claim 1 wherein $R^4$, $R^5$, $R^6$ and $R^7$ are hydrogen, methyl, ethyl, n-propyl, isopropyl, n-butyl, isobutyl, sec-butyl or t-butyl.

4. A compound according to claim 1 wherein Ar is phenyl unsubstituted or substituted by one to three substituents selected from the group consisting of fluoro, chloro, bromo, iodo; straight or branched chain alkyl of 1 to 4 carbon atoms; straight or branched chain alkoxy of 1 to 4 carbon atoms unsubstituted or substituted by lower alkoxy, acetyloxy, amino or mono- or di-lower alkylamino; aralkyloxy of 7 to 9 carbon atoms; straight or branched chain alkenyloxy of 3 to 6 carbon atoms; straight or branched chain alkynyloxy of 3 to 6 carbon atoms; hydroxy; difluoromethoxy; alkylamino of 1 to 4 carbon atoms; methylenedioxy; trifluoromethyl; cyano; alkylthio of 1 to 4 carbon atoms and alkylsulphinyl of 1 to 4 carbon atoms.

5. A compound according to claim 1 in the form of a pharmaceutically acceptable acid addition salt wherein said salt is the hydrochloride, sulphate, nitrate, phosphate, borate, hydrobromate, benzene sulphonate, p-toluene sulphonate, methane sulphonate, ethane sulphonate, naphthalene sulphonate or camphor sulphonate.

6. A compound according to claim 1 wherein $R^2$ is $$-\underset{\underset{R^6}{|}}{C}=\underset{\underset{R^7}{|}}{C}-Ar$$

wherein Ar is phenyl unsubstituted or substituted by one to three substituents selected from the group consisting of halo; lower alkyl; hydroxy; lower alkoxy unsubstituted or substituted by lower alkoxy, acetyloxy, amino or mono- or di-lower alkylamino; aralkyloxy wherein the alkyl moiety is a lower alkyl moiety, lower alkenyloxy; lower alkynyloxy; difluoromethoxy; lower alkylamino; methylenedioxy; trifluoromethyl; cyano; lower alkylthio and lower alkylsulfinyl; $R^6$, and $R^7$ are hydrogen or lower alkyl.

7. The compound according to claim 1 which is methyl (E)-2-(3,4-dimethoxystyryl)benzimidazole-4-carboxylate.

8. The compound according to claim 1 which is the phosphate salt of methyl (E)-2-(3,4-dimethoxystyryl)-benzimidazole-4-carboxylate.

9. A pharmaceutical composition useful for treating ulcers in humans and animals which comprises a therapeutically effective amount of a compound of the formula (I):

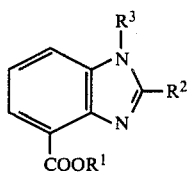   (I)

or a pharmaceutically acceptable acid addition salt thereof wherein $R^1$ is hydrogen or lower alkyl; $R^2$ is

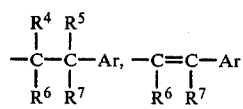

or —C≡C—Ar wherein Ar is phenyl unsubstituted or substituted by one to three substituents selected from the group consisting of:
(a) halo;
(b) lower alkyl;
(c) hydroxy;
(d) lower alkoxy unsubstituted or substituted by lower alkoxy, acetyloxy, amino or mono- or di-lower alkylamino;
(e) aralkyloxy wherein the alkyl moiety is a lower alkyl moiety;
(f) lower alkenyloxy;
(g) lower alkynylloxy;
(h) difluoromethoxy;
(i) lower alkylamino;
(j) methylenedioxy;
(k) trifluoromethyl;
(l) cyano;
(m) lower alkylthio; and
(n) lower alkylsulfinyl;
$R^4$, $R^5$, $R^6$, and $R^7$ are hydrogen or lower alkyl or $R^4$ and $R^5$ together with the carbon atoms to which they are attached form a cyclopropyl ring; and $R^3$ is hydrogen, lower alkyl, acyl or alkylsulphonyl, in combination with a pharmaceutically acceptable carrier.

10. A composition according to claim 9 wherein $R^1$ is hydrogen, methyl, ethyl, n-propyl, isopropyl, n-butyl, isobutyl, sec-butyl or tert-butyl.

11. A composition according to claim 9 wherein $R^4$, $R^5$, $R^6$ and $R^7$ are hydrogen, methyl, ethyl, n-propyl, isopropyl, n-butyl, isobutyl, sec-butyl or t-butyl.

12. A composition according to claim 9 wherein Ar is phenyl unsubstituted or substituted by one to three substitutents selected from the group consisting of fluoro, chloro, bromo, iodo; straight or branched chain alkyl of 1 to 4 carbon atoms; straight or branched chain alkoxy of 1 to 4 carbon atoms; said alkoxy being unsubstituted or substituted by lower alkoxy, acetyloxy amino, mono- or di-lower alkylamino aralkyloxy of 7 to 9 carbon atoms; straight or branched chain alkenyloxy of 3 to 6 carbon atoms; straight or branched chain alkynyloxy of 3 to 6 carbon atoms; hydroxy; diflurormethoxy; alkylamino of 1 to 4 carbon atoms; methylenedioxy; trifluoromethyl; cyano; alkylthio of 1 to 4 carbon atoms and alkylsulphinyl of 1 to 4 carbon atoms.

13. A composition according to claim 9 wherein the compound is in the form of a pharmaceutically acceptable acid addition salt wherein said salt is the hydrochloride, sulphate, nitrate, phosphate, borate, hydrobromate, benzene sulphonate, p-toluene sulphonate, methane sulphonate, ethane sulphonate, naphthalene sulphonate or camphor sulphonate.

14. A composition according to claim 9 wherein $R^2$ is

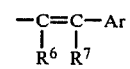

wherein Ar is phenyl unsubstituted or substituted by one of three substituents selected from the group consisting of halo; lower alkyl; hydroxy; lower alkoxy unsubstituted or substituted by lower alkoxy, acetyloxy, amino or mono- or di-lower alkylamino; aralkyloxy wherein the alkyl moiety is a lower alkyl moiety; lower alkenyloxy; lower alkynyloxy; difluoromethoxy; lower alkylamino; methylenedioxy; trifluoromethyl; cyano; lower alkylthio and lower alkylsulfinyl; $R^6$, and $R^7$ are hydrogen or lower alkyl.

15. A composition according to claim 9 wherein the compound is methyl (E)-2-(3,4-dimethoxystyryl)benzimidazole-4-carboxylate.

16. A composition according to claim 9 wherein the compound is the phosphate salt of methyl (E)-2-(3,4-dimethoxystyryl)benzimidazole-4-carboxylate.

17. A method of treating ulcers in humans and animals which comprises administering to a human or animal in need thereof a therapuetically effective amount of a compound of the formula (I):

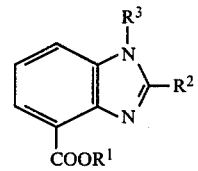   (I)

or a pharmaceutically acceptable acid addition salt thereof wherein $R^1$ is hydrogen or lower alkyl; $R^2$ is

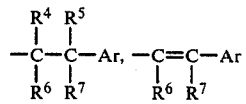

or —C≡—Ar wherein Ar is phenyl unsubstituted or substituted by one to three substituents selected from the group consisting of:
(a) halo;
(b) lower alkyl;
(c) hydroxy;

(d) lower alkoxy unsubstituted or substituted by lower alkoxy, acetyloxy, amino or mono- or di-lower alkylamino;
(e) aralkyloxy wherein the alkyl moiety is a lower alkyl moiety;
(f) lower alkenyloxy;
(g) lower alkynyloxy;
(h) difluoromethoxy;
(i) lower alkylamino;
(j) methylenedioxy;
(k) trifluoromethyl;
(l) cyano;
(m) lower alkylthio; and
(n) lower alkylsulfinyl;

$R^4$, $R^5$, $R^6$, and $R^7$ are hydrogen or lower alkyl or $R^4$ and $R^5$ together with the carbon atoms to which they are attached form a cyclopropyl ring; and $R^3$ is hydrogen, lower alkyl, acyl or alkylsulphonyl, in combination with a pharmaceutically acceptable carrier.

18. A method according to claim 17 wherein $R^1$ is hydrogen, methyl, ethyl, n-propyl, isopropyl, n-butyl, isobutyl, sec-butyl or tert-butyl.

19. A method according to claim 17 wherein $R^4$, $R^5$, $R^6$ and $R^7$ are hydrogen, methyl, ethyl, n-propyl, isopropyl, n-butyl, isobutyl, sec-butyl or t-butyl.

20. A method according to claim 17 wherein Ar is phenyl unsubstituted or substituted by one to three substitutents selected from the group consisting of fluoro, chloro, bromo, iodo; straight or branched chain alkyl of 1 to 4 carbon atoms; straight or branched chain alkoxy of 1 to 4 carbon atoms; said alkoxy being unsubstituted or substituted by lower alkoxy, acetyloxy, amino mono- or di-lower alkylamino aralkyloxy of 7 to 9 carbon atoms; straight or branched chain alkenyloxy of 3 to 6 carbon atoms; straight or branched chain alkynyloxy of 3 to 6 carbon atoms; hydroxy; diflurormethoxy; alkylamino of 1 to 4 carbon atoms; methylenedioxy; trifluoromethyl; cyano; alkylthio of 1 to 4 carbon atoms and alkylsulphinyl of 1 to 4 carbon atoms.

21. A method according to claim 17 wherein the compound is in the form of a pharmaceutically acceptable acid addition salt wherein said salt is the hydrochloride, sulphate, nitrate, phosphate, borate, hydrobromate, benzene sulphonate, p-toluene sulphonate, methane sulphonate, ethane sulphonate, naphthalene sulphonate or camphor sulphonate.

22. A method according to claim 17 wherein $R^2$ is

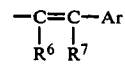

wherein Ar is phenyl unsubstituted or substituted by one to three substituents selected from the group consisting of halo; lower alkyl; hydroxy; lower alkoxy unsubstituted or substituted by lower alkoxy, acetyloxy, amino or mono- or di-lower alkylamino; aralkyloxy wherein the alkyl moiety is a lower alkyl moiety; lower alkenyloxy; lower alkynyloxy; difluoromethoxy; lower alkylamino; methylenedioxy; trifluoromethyl; cyano; lower alkylthio and lower alkylsulfinyl; $R^6$, and $R^7$ are hydrogen or lower alkyl.

23. A method according to claim 17 wherein the compound is methyl (E)-2-(3,4-dimethoxystyryl)benzimidazole-4-carboxylate.

24. A method according to claim 7 where the compound is the phosphate salt of methyl (E)-2-(3,4-dimethoxystyryl)benzimidazole-4-carboxylate.

* * * * *